US008900636B2

(12) United States Patent
Cook

(10) Patent No.: US 8,900,636 B2
(45) Date of Patent: Dec. 2, 2014

(54) CONTROLLED RELEASE COMPOSITIONS

(75) Inventor: Gary P. Cook, Longmont, CO (US)

(73) Assignee: Evonik Corporation, Parsippany, NJ (US)

( * ) Notice: Subject to any disclaimer, the term of this patent is extended or adjusted under 35 U.S.C. 154(b) by 1457 days.

(21) Appl. No.: 10/565,401

(22) PCT Filed: Jul. 15, 2004

(86) PCT No.: PCT/US2004/022817
§ 371 (c)(1),
(2), (4) Date: Jan. 20, 2006

(87) PCT Pub. No.: WO2005/009357
PCT Pub. Date: Feb. 3, 2005

(65) Prior Publication Data
US 2007/0092574 A1 Apr. 26, 2007

Related U.S. Application Data

(60) Provisional application No. 60/489,402, filed on Jul. 23, 2003.

(51) Int. Cl.
A61K 9/14 (2006.01)
A61K 9/16 (2006.01)
A61K 47/48 (2006.01)
A61K 38/28 (2006.01)
A61K 9/50 (2006.01)
A61K 38/31 (2006.01)
A61K 38/11 (2006.01)
A61K 31/715 (2006.01)
A61K 9/51 (2006.01)
A61K 38/09 (2006.01)

(52) U.S. Cl.
CPC ......... A61K 9/1694 (2013.01); A61K 47/48215 (2013.01); A61K 9/1647 (2013.01); A61K 38/28 (2013.01); A61K 9/5031 (2013.01); A61K 38/31 (2013.01); A61K 38/11 (2013.01); A61K 31/715 (2013.01); A61K 9/5153 (2013.01); A61K 38/09 (2013.01); A61K 47/4803 (2013.01)
USPC .......................................... 424/490; 424/489

(58) Field of Classification Search
None
See application file for complete search history.

(56) References Cited

U.S. PATENT DOCUMENTS

| 3,664,963 | A | | 5/1972 | Pasin |
| 3,780,195 | A | | 12/1973 | Balassa |
| 3,790,905 | A | | 2/1974 | Schuttloffel |
| 3,865,352 | A | | 2/1975 | Nelson et al. |
| 3,891,570 | A | | 6/1975 | Fukushima |
| 4,165,219 | A | | 8/1979 | Huber |
| 4,171,981 | A | * | 10/1979 | Austin et al. ................. 106/14.5 |
| 4,183,681 | A | | 1/1980 | Li |
| 4,299,501 | A | | 11/1981 | Patil |
| 4,384,975 | A | | 5/1983 | Fong |
| 4,389,330 | A | | 6/1983 | Tice |
| 4,897,268 | A | | 1/1990 | Tice |
| 4,933,105 | A | | 6/1990 | Fong |
| 5,112,604 | A | | 5/1992 | Beaurline et al. ............. 424/490 |
| 5,407,609 | A | | 4/1995 | Tice |
| 5,534,269 | A | | 7/1996 | Igari et al. |
| 5,538,739 | A | * | 7/1996 | Bodmer et al. ............... 424/501 |
| 5,629,277 | A | | 5/1997 | Plishka ........................ 510/202 |
| 5,654,008 | A | | 8/1997 | Herbert |
| 5,733,566 | A | | 3/1998 | Lewis ........................... 424/426 |
| 5,776,885 | A | | 7/1998 | Orsolini et al. |
| 5,814,342 | A | | 9/1998 | Okada et al. .................. 424/493 |
| 5,846,562 | A | | 12/1998 | Yanai et al. ................... 424/451 |
| 5,869,103 | A | | 2/1999 | Yeh et al. ...................... 424/501 |
| 5,876,761 | A | * | 3/1999 | Bodmer et al. ............... 424/501 |
| 6,120,805 | A | | 9/2000 | Spenlehauer et al. ........ 424/489 |
| 6,140,040 | A | | 10/2000 | Palm et al. ........................ 435/2 |
| 6,194,006 | B1 | | 2/2001 | Lyons et al. .................. 424/489 |
| 6,217,893 | B1 | * | 4/2001 | Pellet et al. ................... 424/426 |
| 6,270,700 | B1 | | 8/2001 | Ignatious |
| 6,281,254 | B1 | | 8/2001 | Nakajima |
| 6,290,983 | B1 | | 9/2001 | Rickey .......................... 424/426 |
| 6,369,121 | B1 | | 4/2002 | Catalfamo et al. .............. 521/64 |
| 6,379,704 | B2 | | 4/2002 | Wright ......................... 424/489 |
| 6,440,493 | B1 | | 8/2002 | Gibson et al. ............. 427/213.3 |
| 6,706,289 | B2 | | 3/2004 | Lewis |

(Continued)

FOREIGN PATENT DOCUMENTS

AU 2004259209 2/2005
CN 101410174 4/2009

(Continued)

OTHER PUBLICATIONS

International Preliminary Report on Patentability Chapter I, PCT/US2004/011485, Feb. 24, 2009.
International Search Report, PCT/US2004/011485, Mar. 21, 2008.
Written Opinion, PCT/US2004/011485, Mar. 21, 2008.
International Preliminary Report on Patentability Chapter I, PCT/US2004/022817, Feb. 2, 2006.
International Search Report, PCT/US2004/022817, Oct. 14, 2005.
Written Opinion, PCT/US2004/022817, Oct. 14, 2005.
International Search Report, PCT/US2004/022816, Jun. 9, 2005.
International Preliminary Report on Patentability Chapter 1, PCT/US2004/022816, Jan. 26, 2006.
Written Opinion, PCT/US2004/022816, Apr. 7, 2005.

(Continued)

Primary Examiner — Susan Tran
(74) Attorney, Agent, or Firm — Linda S. Li; Jason S. Ngui

(57) ABSTRACT

The compositions disclosed herein are for use as controlled release therapeutics for the treatment of a wide variety of diseases. In particular, the compositions provide water soluble bioactive agents, organic ions and polymers where the bioactive agent is efficiently released over time with minimal degradation products. The resulting controlled release composition is capable of administration in a decreased dose volume due to the high drug content and predominance of non-degraded bioactive agent after release. Additionally, the compositions of the present invention are capable of long term, sustained releases.

13 Claims, No Drawings

(56) References Cited

U.S. PATENT DOCUMENTS

| | | | |
|---|---|---|---|
| 6,740,634 B1 | 5/2004 | Saikawa et al. | |
| 6,953,593 B2 | 10/2005 | Juhrts | |
| 7,265,157 B1* | 9/2007 | Igari et al. | 514/772.1 |
| 7,388,032 B2 | 6/2008 | Saikawa et al. | |
| 2001/0035352 A1 | 11/2001 | Ozerov | 204/549 |
| 2002/0025329 A1 | 2/2002 | O'Hagan et al. | 424/278.1 |
| 2002/0028216 A1 | 3/2002 | Donovan | 424/236.1 |
| 2002/0142050 A1 | 10/2002 | Straub et al. | |
| 2002/0155158 A1 | 10/2002 | Lewis et al. | |
| 2003/0134800 A1* | 7/2003 | Yamamoto et al. | 514/16 |
| 2006/0228414 A1 | 10/2006 | Cook | |
| 2007/0092574 A1 | 4/2007 | Cook | |
| 2007/0190154 A1 | 8/2007 | Ziegerson | |
| 2007/0207211 A1 | 9/2007 | Ziegerson | |

FOREIGN PATENT DOCUMENTS

| | | |
|---|---|---|
| CN | 102935069 | 2/2013 |
| EP | 1829529 | 9/2007 |
| EP | 2548550 | 1/2013 |
| JP | 01-108976 A | 4/1989 |
| JP | 10-109024 | 4/1998 |
| JP | 10-273447 A | 10/1998 |
| JP | 11-349688 | 12/1999 |
| WO | WO-91/15193 A1 | 10/1991 |
| WO | WO 95/13799 | 5/1995 |
| WO | WO 97/04747 | 2/1997 |
| WO | WO 97/41837 | 11/1997 |
| WO | WO9832423 | 7/1998 |
| WO | WO 98/43660 | 10/1998 |
| WO | WO-99/36099 A1 | 7/1999 |
| WO | WO 00/62761 | 10/2000 |
| WO | WO-00/62761 A1 | 10/2000 |
| WO | WO 0105380 A1 * | 1/2001 |
| WO | WO 01/34120 | 5/2001 |
| WO | WO-02/36169 A2 | 5/2002 |
| WO | WO 0241765 A2 * | 5/2002 |
| WO | WO-02/061469 A2 | 8/2002 |
| WO | WO 02058672 A2 * | 8/2002 |
| WO | WO-03/002092 A2 | 1/2003 |
| WO | WO03092585 | 11/2003 |
| WO | WO2004078147 | 9/2004 |
| WO | WO 2004/091494 | 10/2004 |
| WO | WO 2005/003180 | 1/2005 |
| WO | WO2005003180 | 1/2005 |
| WO | WO 2005/009356 | 2/2005 |
| WO | WO 2005/009356 A3 | 2/2005 |
| WO | WO 2005/009357 | 2/2005 |
| WO | WO2005009357 | 2/2005 |

OTHER PUBLICATIONS

Langer, "Drug delivery and targeting," Nature 392(Supplement):5-10 (1998).
Franssen, O., WE Hennick "A Novel Preparation Method for Polymeric Microparticles Without the Use of Organic Solvents". International Journal of Pharmaceutics 168 (1998) 1-7.
PL Johnson, "Metal Safety Data Sheet, Sorbitol 70% Solution." Paddock Laboratories Inc. Minneapolis, MN, USA. Dec. 10, 1991.
Materials Safety Data Sheet, Sodium Cholate. Sciencelab.com. Nov. 6, 2008, 6 pages.
Buwalda, R. "Molecular Aggregation in Water the Interplay of Hydrophobic and Electrostatic Interactions." University of Groningen, Doctoral Dissertation, Nov. 19, 2001. Table of Contents only. 10 pages.
Buwalda, R. "Molecular Aggregation in Water the Interplay of Hydrophobic and Electrostatic Interactions." "Chapter 5 Wormlike Micellar and Vesicular Phases in Aqueous Solutions of Single-Tailed Surfactants with Aromatic Counter Ions." Nov. 19, 2001, pp. 97-118.
Notice of Acceptance issued by Australian IP Office on Mar. 22, 2010 for AU Pat. App. No. 2004253853, which is national phase of Intl. Pat. App. No. PCT/US2004/011485 filed Apr. 12, 2004 (Inventor—Ziegerson; Applicant—PR Pharmaceuticals; pp. 1-3).
Examiner's Report issued by Australian IP Office on Feb. 24, 2010 for AU Pat. App. No. 2004253853, which is national phase of Intl. Pat. App. No. PCT/US2004/011485 filed Apr. 12, 2004 (Inventor—Ziegerson; Applicant—PR Pharmaceuticals; pp. 1-2).
Response to Office Action filed by Applicant on Jan. 18, 2010 for AU Pat. App. No. 2004253853, which is national phase of Intl. Pat. App. No. PCT/US2004/011485 filed Apr. 12, 2004 (Inventor—Ziegerson; Applicant—PR Pharmaceuticals; pp. 1-15).
Examiner's Report issued by Australian IP Office on Sep. 9, 2009 for AU Pat. App. No. 2004253853, which is national phase of Intl. Pat. App. No. PCT/US2004/011485 filed Apr. 12, 2004 (Inventor—Ziegerson; Applicant—PR Pharmaceuticals; pp. 1-2).
Response to Office Action filed by Applicant on Aug. 15, 2011 for CA Pat. App. No. 2,516,107, which is national phase of Intl. Pat. App. No. PCT/US2004/011485 filed Apr. 12, 2004 (Inventor—Ziegerson; Applicant—PR Pharmaceuticals; pp. 1-17).
Office Action issued by Canandian IP Office on Feb. 16, 2011 for CA Pat. App. No. 2,516,107, which is national phase of Intl. Pat. App. No. PCT/US2004/011485 filed Apr. 12, 2004 (Inventor—Ziegerson; Applicant—PR Pharmaceuticals; pp. 1-2).
Certificate of Patent issued on Apr. 6, 2011 for CN Pat. App. No. 2004800008408.8, which is national phase of Intl. Pat. App. No. PCT/US2004/011485 filed Apr. 12, 2004 (Inventor—Ziegerson; Applicant—PR Pharmaceuticals; pp. 1-17).
Response to Office Action filed on Sep. 3, 2010 for CN Pat. App. No. 2004800008408.8, which is national phase of Intl. Pat. App. No. PCT/US2004/011485 filed Apr. 12, 2004 (Inventor—Ziegerson; Applicant—PR Pharmaceuticals; pp. 1-5).
Response to Office Action filed on Apr. 22, 2010 for CN Pat. App. No. 2004800008408.8, which is national phase of Intl. Pat. App. No. PCT/US2004/011485 filed Apr. 12, 2004 (Inventor—Ziegerson; Applicant—PR Pharmaceuticals; pp. 1-8).
Response to Office Action filed on Jan. 15, 2010 for CN Pat. App. No. 2004800008408.8, which is national phase of Intl. Pat. App. No. PCT/US2004/011485 filed Apr. 12, 2004 (Inventor—Ziegerson; Applicant—PR Pharmaceuticals; pp. 1-8).
Office Action issued on Oct. 23, 2009 for CN Pat. App. No. 2004800008408.8, which is national phase of Intl. Pat. App. No. PCT/US2004/011485 filed Apr. 12, 2004 (Inventor—Ziegerson; Applicant—PR Pharmaceuticals; pp. 1-6).
Preliminary Amendment filed on Aug. 17, 2009 for CN Pat. App. No. 2004800008408.8, which is national phase of Intl. Pat. App. No. PCT/US2004/011485 filed Apr. 12, 2004 (Inventor—Ziegerson; Applicant—PR Pharmaceuticals; pp. 1-14).
Communication from Examining Division issued on Jul. 19, 2011 for EP Pat. App. No. 04750117.6, which is national phase of Intl. Pat. App. No. PCT/US2004/011485 filed Apr. 12, 2004 (Inventor—Ziegerson; Applicant—PR Pharmaceuticals; pp. 1-7).
Supplemental Search Report issued on Oct. 28, 2009 for EP Pat. App. No. 04750117.6, which is national phase of Intl. Pat. App. No. PCT/US2004/011485 filed Apr. 12, 2004 (Inventor—Ziegerson; Applicant—PR Pharmaceuticals; pp. 1-3).
Preliminary Amendment filed on Dec. 30, 2005 for EP Pat. App. No. 04750117.6, which is national phase of Intl. Pat. App. No. PCT/US2004/011485 filed Apr. 12, 2004 (Inventor—Ziegerson; Applicant—PR Pharmaceuticals; pp. 1-6).
Indian Letters Patent Document issued on Apr. 29, 2010 for IN Pat. App. No. 4743/DELNP/2005, which is national phase of Intl. Pat. App. No. PCT/US2004/011485 filed Apr. 12, 2004 (Inventor—Ziegerson; Applicant—PR Pharmaceuticals; pp. 1).
Response to Examination Report filed on Dec. 30, 2009 for IN Pat. App. No. 4743/DELNP/2005, which is national phase of Intl. Pat. App. No. PCT/US2004/011485 filed Apr. 12, 2004 (Inventor—Ziegerson; Applicant—PR Pharmaceuticals; pp. 1-7).
Examination Report issued on Jan. 14, 2009 for IN Pat. App. No. 4743/DELNP/2005, which is national phase of Intl. Pat. App. No. PCT/US2004/011485 filed Apr. 12, 2004 (Inventor—Ziegerson; Applicant—PR Pharmaceuticals; pp. 1-2).
Final Office Action issued on Apr. 2, 2010 for JP Pat. App. No. 2006-532408, which is national phase of Intl. Pat. App. No. PCT/US2004/011485 filed Apr. 12, 2004 (Inventor—Ziegerson; Applicant—PR Pharmaceuticals; pp. 1-2).

(56) References Cited

OTHER PUBLICATIONS

Response to Office Action filed on Dec. 25, 2009 for JP Pat. App. No. 2006-532408, which is national phase of Intl. Pat. App. No. PCT/US2004/011485 filed Apr. 12, 2004 (Inventor—Ziegerson; Applicant—PR Pharmaceuticals; pp. 1-12).
Office Action issued on Aug. 31, 2009 for JP Pat. App. No. 2006-532408, which is national phase of Intl. Pat. App. No. PCT/US2004/011485 filed Apr. 12, 2004 (Inventor—Ziegerson; Applicant—PR Pharmaceuticals; pp. 1-3).
Preliminary Amendment filed on Jul. 26, 2010 for JP Pat. App. No. 2009-296315, which is which is divisional of JP Pat. App. No. 2006-532408, filed Apr. 12, 2004 (Inventor—Ziegerson; Applicant—PR Pharmaceuticals; pp. 1-8).
Response to Final Office Action/Request for Continued Examination filed by Applicant on May 5, 2010 for U.S. Appl. No. 11/799,700, filed May 1, 2007 (Inventor—Zeigerson; pp. 1-8).
Final Office Action issued on Jan. 5, 2010 by USPTO for U.S. Appl. No. 11/799,700, filed May 1, 2007 (Invento—Zeigerson; pp. 1-11).
Response to Non-Final Office Action filed on Aug. 27, 2009 for U.S. Appl. No. 11/799,700, filed May 1, 2007 (Inventor—Zeigerson; pp. 1-9).
Non-Final Office Action issued on Apr. 29, 2009 by USPTO for U.S. Appl. No. 11/799,700, filed May 1, 2007 (Inventor—Zeigerson; pp. 1-12).
Response to Restriction Requirement filed on Feb. 9, 2009 for U.S. Appl. No. 11/799,700, filed May 1, 2007 (Inventor—Zeigerson; pp. 1-10).
Restriction Requirement issued by USPTO on Jan. 12, 2009 for U.S. Appl. No. 11/799,700, filed May 1, 2007 (Inventor—Zeigerson; pp. 1-7).
Response to Restriction Requirement filed on Oct. 21, 2008 for U.S. Appl. No. 11/799,700, filed May 1, 2007 (Inventor—Zeigerson; pp. 1-10).
Restriction Requirement issued by USPTO on Apr. 21, 2008 for U.S. Appl. No. 11/799,700, filed May 1, 2007 (Inventor—Zeigerson; pp. 1-11).
Office Action issued by Canadian IP Office on Feb. 8, 2011 for CA Pat. App. No. 2,533,592, which is national phase of Intl. App. No. PCT/US2004/022817, filed on Jul. 15, 2004 (Inventor—Cook; Applicant—PR Pharmaceuticals; pp. 1-3).
Decision of Granting Patent Right issued on Oct. 16, 2009 for CN Pat. App. No. 200480027243.9, which is national phase of Intl. App. No. PCT/US2004/022817, filed on Jul. 15, 2004 (Inventor—Cook; Applicant—PR Pharmaceuticals; pp. 1-2).
Request for Reexamination filed on Jun. 15, 2009 for CN Pat. App. No. 200480027243.9, which is national phase of Intl. App. No. PCT/US2004/022817, filed on Jul. 15, 2004 (Inventor—Cook; Applicant—PR Pharmaceuticals; pp. 1-11).
Office Action issued on Feb. 27, 2009 for CN Pat. App. No. 200480027243.9, which is national phase of Intl. App. No. PCT/US2004/022817, filed on Jul. 15, 2004 (Inventor—Cook; Applicant—PR Pharmaceuticals; pp. 1-4).
Response to Office Action filed on Mar. 24, 2008 for CN Pat. App. No. 200480027243.9, which is national phase of Intl. App. No. PCT/US2004/022817, filed on Jul. 15, 2004 (Inventor—Cook; Applicant—PR Pharmaceuticals; pp. 1-4).
First Office Action issued on Oct. 19, 2007 for CN Pat. App. No. 200480027243.9, which is national phase of Intl. App. No. PCT/US2004/022817, filed on Jul. 15, 2004 (Inventor—Cook; Applicant—PR Pharmaceuticals; pp. 1-6).
Communication from Examining Division issued on Jan. 11, 2011 for EP Pat. App. No. 04778361.8, which is national phase of Intl. App. No. PCT/US2004/022817, filed on Jul. 15, 2004 (Inventor—Cook; Applicant—PR Pharmaceuticals; pp. 1-6).
Reply to Communication from Examining Division filed on Apr. 29, 2010 for EP Pat. App. No. 04778361.8, which is national phase of Intl. App. No. PCT/US2004/022817, filed on Jul. 15, 2004 (Inventor—Cook; Applicant—PR Pharmaceuticals; pp. 1-7).
Communication from Examining Division issued on Oct. 22, 2009 for EP Pat. App. No. 04778361.8, which is national phase of Intl. App. No. PCT/US2004/022817, filed on Jul. 15, 2004 (Inventor—Cook; Applicant—PR Pharmaceuticals; pp. 1-6).
Supplemental European Search Report issued on Jun. 10, 2009 for EP Pat. App. No. 04778361.8, which is national phase of Intl. App. No. PCT/US2004/022817, filed on Jul. 15, 2004 (Inventor—Cook; Applicant—PR Pharmaceuticals; pp. 1-3).
Preliminary Amendment filed on Apr. 24, 2006 for EP Pat. App. No. 04778361.8, which is national phase of Intl. App. No. PCT/US2004/022817, filed on Jul. 15, 2004 (Inventor—Cook; Applicant—PR Pharmaceuticals; pp. 1-11).
Request for Hearing filed on Apr. 15, 2009 for IN Pat. App. No. 957/DELNP/2006, which is national phase of Intl. App. No. PCT/US2004/022817, filed on Jul. 15, 2004 (Inventor—Cook; Applicant—PR Pharmaceuticals; pp. 1).
Response to Examination Report filed on Mar. 25, 2009 for IN Pat. App. No. 957/DELNP/2006, which is national phase of Intl. App. No. PCT/US2004/022817, filed on Jul. 15, 2004 (Inventor—Cook; Applicant—PR Pharmaceuticals; pp. 1-16).
Examination Report issued on Apr. 15, 2008 for IN Pat. App. No. 957/DELNP/2006, which is national phase of Intl. App. No. PCT/US2004/022817, filed on Jul. 15, 2004 (Inventor—Cook; Applicant—PR Pharmaceuticals; pp. 1-2).
Response to Office Action filed on Apr. 28, 2011 for JP Pat App. No. 2006-521134, which is national phase of Intl. App. No. PCT/US2004/022817, filed on Jul. 15, 2004 (Inventor—Cook; Applicant—PR Pharmaceuticals; pp. 1-5).
Office Action issued on Nov. 1, 2010 for JP Pat App. No. 2006-521134, which is national phase of Intl. App. No. PCT/US2004/022817, filed on Jul. 15, 2004 (Inventor—Cook; Applicant—PR Pharmaceuticals; pp. 1-9).
Response to Non-Final Office Action filed on Mar. 17, 2010 for for U.S. Appl. No. 10/564,494, filed Jul. 15, 2004 (Inventor—Cook; pp. 1-12).
Non-Final Office Action issued by USPTO on Nov. 19, 2009 for for U.S. Appl. No. 10/564,494, filed Jul. 15, 2004 (Inventor—Cook; pp. 1-13).
Response to Non-Final Office Action filed on Oct. 13, 2009 for for U.S. Appl. No. 10/564,494, filed Jul. 15, 2004 (Inventor—Cook; pp. 1-14).
Non-Final Office Action issued by USPTO on Apr. 16, 2009 for for U.S. Appl. No. 10/564,494, filed Jul. 15, 2004 (Inventor—Cook; pp. 1-15).
Response to Restriction Requirement filed on Feb. 9, 2009 for for U.S. Appl. No. 10/564,494, filed Jul. 15, 2004 (Inventor—Cook; pp. 1-13).
Restriction Requirement issued by USPTO on Dec. 8, 2009 for for U.S. Appl. No. 10/564,494, filed Jul. 15, 2004 (Inventor—Cook; pp. 1-11).
Examination Response filed on Apr. 13, 2011 for AU Pat. App. No. 2004259208, which is national phase of Intl. App. No. PCT/US2004/022816, filed on Jul. 15, 2004 (Inventor—Cook; Applicant—PR Pharmaceuticals; pp. 1-3).
Examiner's Report issued by Australian IP Office on Apr. 8, 2011 for AU Pat. App. No. 2004259208, which is national phase of Intl. App. No. PCT/US2004/022816, filed on Jul. 15, 2004 (Inventor—Cook; Applicant—PR Pharmaceuticals; pp. 1).
Examiner's Report issued by Australian IP Office on Aug. 3, 2009 for AU Pat. App. No. 2004259208, which is national phase of Intl. App. No. PCT/US2004/022816, filed on Jul. 15, 2004 (Inventor—Cook; Applicant—PR Pharmaceuticals; pp. 1-2).
Office Action issued by Canadian IP Office on Apr. 27, 2011 for CA Pat. App. No. 2,533,302, which is national phase of Intl. App. No. PCT/US2004/022816, filed on Jul. 15, 2004 (Inventor—Cook; Applicant—PR Pharmaceuticals; pp. 1-3).
Response to Office Action filed on Jan. 21, 2010 for CN Pat. App. No. 200480026606.7, which is national phase of Intl. App. No. PCT/US2004/022816, filed on Jul. 15, 2004 (Inventor—Cook; Applicant—PR Pharmaceuticals; pp. 1-10).
Office Action issued on Jul. 17, 2009 for CN Pat. App. No. 200480026606.7, which is national phase of Intl. App. No. PCT/US2004/022816, filed on Jul. 15, 2004 (Inventor—Cook; Applicant—PR Pharmaceuticals; pp. 1-15).

(56) References Cited

OTHER PUBLICATIONS

Communication from Examining Division issued on Jan. 11, 2011 for EP Pat App. No. 04778360.0, which is national phase of Intl. App. No. PCT/US2004/022816, filed on Jul. 15, 2004 (Inventor—Cook; Applicant—PR Pharmaceuticals; pp. 1-6).
Reply to Communication filed on Apr. 29, 2010 for EP Pat App. No. 04778360.0, which is national phase of Intl. App. No. PCT/US2004/022816, filed on Jul. 15, 2004 (Inventor—Cook; Applicant—PR Pharmaceuticals; pp. 1-9).
Communication from Examining Division issued on Oct. 22, 2009 for EP Pat App. No. 04778360.0, which is national phase of Intl. App. No. PCT/US2004/022816, filed on Jul. 15, 2004 (Inventor—Cook; Applicant—PR Pharmaceuticals; pp. 1-7).
Supplementary European Search Report issued on Jun. 10, 2009 for EP Pat App. No. 04778360.0, which is national phase of Intl. App. No. PCT/US2004/022816, filed on Jul. 15, 2004 (Inventor—Cook; Applicant—PR Pharmaceuticals; pp. 1-3).
Preliminary Amendment filed on Apr. 13, 2006 for EP Pat App. No. 04778360.0, which is national phase of Intl. App. No. PCT/US2004/022816, filed on Jul. 15, 2004 (Inventor—Cook; Applicant—PR Pharmaceuticals; pp. 1-7).
Indian Letters Patent Document issued on Jan. 29, 2009 for IN Pat. App. No. No. 706/DELNP/2006, which is national phase of Intl. App. No. PCT/US2004/022816, filed on Jul. 15, 2004 (Inventor—Cook; Applicant—PR Pharmaceuticals; pp. 1).
Supplemental Response to Examination Report filed on Jan. 9, 2009 for IN Pat. App. No. No. 706/DELNP/2006, which is national phase of Intl. App. No. PCT/US2004/022816, filed on Jul. 15, 2004 (Inventor—Cook; Applicant—PR Pharmaceuticals; pp. 1-2).
Response to Examination Report filed on Jan. 9, 2009 for IN Pat. App. No. No. 706/DELNP/2006, which is national phase of Intl. App. No. PCT/US2004/022816, filed on Jul. 15, 2004 (Inventor—Cook; Applicant—PR Pharmaceuticals; pp. 1-4).
Examination Report issued on Jan. 11, 2008 for IN Pat. App. No. No. 706/DELNP/2006, which is national phase of Intl. App. No. PCT/US2004/022816, filed on Jul. 15, 2004 (Inventor—Cook; Applicant—PR Pharmaceuticals; pp. 1-2).
Response to Office Action filed on Apr. 27, 2011 for JP Pat App. No. 2006-520347, which is national phase of Intl. App. No. PCT/US2004/022816, filed on Jul. 15, 2004 (Inventor—Cook; Applicant—PR Pharmaceuticals; pp. 1-5).
Office Action issued on Nov. 1, 2010 for JP Pat App. No. 2006-520347, which is national phase of Intl. App. No. PCT/US2004/022816, filed on Jul. 15, 2004 (Inventor—Cook; Applicant—PR Pharmaceuticals; pp. 1-7).
Response to Non-Final Office Action filed by Applicant on Apr. 14, 2009 for U.S. Appl. No. 10/553,003, filed Apr. 12, 2004 (Inventor—Zeigerson; pp. 1-9).
Non-Final Office Action issued by USPTO on Dec. 9, 2009 for U.S. Appl. No. 10/553,003, filed Apr. 12, 2004 (Inventor—Zeigerson; pp. 1-14).
Response to Restriction Requirement filed by Applicant on Oct. 5, 2009 for U.S. Appl. No. 10/553,003, filed Apr. 12, 2004 (Inventor—Zeigerson; pp. 1-5).
Restriction Requirement issued by USPTO on Jul. 1, 2009 for U.S. Appl. No. 10/553,003, filed Apr. 12, 2004 (Inventor—Zeigerson; pp. 1-5).
Mohr, W.D. et al., "Mixing in Laminar-Flow Systems," 1957, ACS, Industrial and Engineering Chemistry, vol. 49, No. 11.
Mott, Robert L., "Applied Fluid Mechanics," 1972, Charles E. Merrill Publishing.
Smith et al., "Evaluation of poly(lactic acid) as a biodegradable drug delivery system for parenteral administration," Intl. J. Pharm. 30:215-220, 1986.
Harnby et al. editors, "Mixing in the Process Industries," 1992, Butterworth & Heinemann; Second Edition, Chapter 12; Godfrey JC, "Static Mixers".
Rothen-Weinhold et al., "Development and evaluation in vivo of a long-term delivery system for vapreotide, a somatostatin analog," 1998, J. Contr. Rel. 52.

Rothen-Weinhold et al., "Stability studies of a somatostatin analogue in biodegradable implants," 1999, Intl. J. Pharm. 178.
Maa, Y.F. and Hsu, C., "Liquid-Liquid emulsification by static mixers for use in microencapsulation," 1996, Taylor & Francis, Journal of Microencapsulation, vol. 13, No. 4.
Crooks, Richard M. & Seong, Gi Hun, "Efficient Mixing and Reactions within Microfluidic Channels Using Microbead-Supported Catalysts," 2002, ACS, Journal of the American Chemical Society, vol. 124, No. 45.
Yanai et al., "Optimal Formulation of an Angiogenesis Inhibitor, TNP-470, for Arterial Injection Determined by In Vitro Drug Release and Stability, and In Vivo Activity," International Journal of Pharmaceuticals 123 (1995).
Edlund and Albertson, "Degradable polymer microspheres for controlled drug delivery," In: Advances in Polymer Science, Abe et al. Ed., Springer-Verlag, Heidleberg, 2002, discloses many different methods for preparing microparticles.
Office Action dated Feb. 12, 2010 from State Intellectual Property Office of the Peoples Republic of China Application No. 2004800008408.8.
Office Action dated Jun. 18, 2010 from State Intellectual Property Office of the Peoples Republic of China Application No. 2004800008408.8.
Final Office Action dated Aug. 3, 2010 from U.S. Appl. No. 10/553,003.
Response to Final Office Action dated Nov. 3, 2010 from U.S. Appl. No. 10/553,003.
Preliminary Amendment dated Oct. 10, 2005 from U.S. Appl. No. 10/553,003.
Final Office Action dated May 26, 2010 from U.S. Appl. No. 10/564,494.
Response to Final Office Action dated Nov. 22, 2010 from U.S. Appl. No. 10/564,494.
Response to Office Action dated Sep. 14, 2010 from Europe Application 04750117.6.
Office Action dated Mar. 4, 2010 from European Patent Application No. 04750117.6.
Reply to Communication from Examining Division filed on Nov. 29, 2011 for EP Pat. App. No. 04750117.6, which is national phase of Intl. Pat. App. No. PCT/US2004/011485 filed Apr. 12, 2004 (Inventor—Ziegerson; Applicant—PR Pharmaceuticals; pp. 1-15).
Office Action issued on Dec. 16, 2011 for JP Pat App. No. 2006-521134, which is national phase of Intl. App. No. PCT/US2004/022817, filed on Jul. 15, 2004 (Inventor—Cook; Applicant—PR Pharmaceuticals; pp. 1-5).
Response to Office Action filed on Oct. 26, 2011 for CA Pat. App. No. 2,533,302, which is national phase of Intl. App. No. PCT/US2004/022816, filed on Jul. 15, 2004 (Inventor—Cook; Applicant—PR Pharmaceuticals; pp. 1-15).
Office Action issued on Dec. 23, 2011 for CN Pat. App. No. 200480026606.7, which is national phase of Intl. App. No. PCT/US2004/022816, filed on Jul. 15, 2004 (Inventor—Cook; Applicant—PR Pharmaceuticals; pp. 1-11).
Non-Final Office Action issued on May 31, 2013 for U.S. Appl. No. 10/553,003, filed Apr. 12, 2004 (Inventor—Zeigerson; pp. 1-18).
Hovekamp; "Experimental and Numerical Investigation of Porous Media Flow with regard to the Emulsion Process," 2002, A doctoral dissertation submitted to the Swiss Federal Institute of Technology Zurich, pp. 1-101.
Final Office Action issued on May 10, 2013 by USPTO for U.S. Appl. No. 11/799,700, filed May 1, 2007 (Inventor—Zeigerson; pp. 1-21).
Non-Final Office Action issued by USPTO on May 2, 2013 for for U.S. Appl. No. 10/564,494, filed Jul. 15, 2004 (Inventor—Cook; pp. 1-17).
CAS Registry Records for 25832-58-0, 532-02-5, 2169-87-1, 18396-51-5, 14206-62-3, 17273-79-9, 23520-54-9. All entered STN Nov. 16, 1984. 7 pages.
RJ Podolsky. "The Structure of Water and Electrolyte Solutions." Circulation, vol. 21, May 1960, pp. 818-827.
Final Office Action issued by USPTO on Aug. 9, 2013 for for U.S. Appl. No. 10/564,494, filed Jul. 15, 2004 (Inventor —Cook; pp. 1-20).

(56) References Cited

OTHER PUBLICATIONS

Defintion of "perforated" retrieved from <www.dictionary.com> on Mar. 30, 2013, p. 1.
Carrasquillo, K.G. et al., Controlled Delivery of the Anti-VEGF Aptamer EYE001 with Poly(lactic-co-glycolic) Acid Microspheres, Invest. Opthalmol. Vis. Sci., Jan. 2003, Vo. 44, No. 1, pp. 290-299.
Kobayashi, I. et al., "Silicon Array of Elongated Through-Holes for Monodisperse Emulsion Droplets," AIChE Journal, Aug. 2002, vol. 48, No. 8, pp. 1639-1644.
Response to Office Action filed on Mar. 8, 2013 for CA Pat. App. No. 2,516,107, which is a national phase of Intl. Pat. App. No. PCT/US2004/011485, filed on Apr. 12, 2004 [Inventor—Ziegerson; Applicant—PR Pharmaceuticals] [7 pages].
Office Action issued on Sep. 12, 2012 for CA Pat. App. No. 2,516,107, which is a national phase of Intl. Pat. App. No. PCT/US2004/011485, filed on Apr. 12, 2004 [Inventor—Ziegerson; Applicant—PR Pharmaceuticals] [2 pages].
English translation of Office Action issued on Dec. 19, 2012 for CN Pat. App. No. 201110028030.X, which is divisional of CN Pat. App. No. 2004800008408.8, national phase of Intl. Pat. App. No. PCT/US2004/011485 filed Apr. 12, 2004 [Inventor—Ziegerson; Applicant—PR Pharmaceuticals] [8 pages].
Intention to Grant European Patent issued on Oct. 26, 2012 for EP Pat. App. No. 04750117.6, which is a national phase of Intl. Pat. App. No. PCT/US2004/011485 filed on Apr. 12, 2004 [Inventor—Ziegerson; Applicant—PR Pharmaceuticals] [35 pages].
Extended European Search Report issued on Jan. 4, 2013 for EP Pat. App. No. 12159499.8, which was filed on Mar. 14, 2012 [Inventor—Ziegerson; Applicant—Surmodics Pharmaceuticals, Inc.] [8 pages].
Final Official Action issued on Mar. 4, 2013 for JP Pat. App. No. 2009-296315, with is a Divisional of JP Pat. App. No. 2006-532408, national phase of Intl. Pat. App. No. PCT/US2004/011485, filed on Apr. 12, 2004 [Inventor—Ziegerson; Applicant—PR Pharmaceuticals] [2 pages].
Official Action issued on Aug. 31, 2012 for JP Pat. App. No. 2009-296315, which is a divisional of JP Pat. App. No. 2006-532408, national phase of Intl. Pat. App. No. PCT/US2004/011485, filed on Apr. 12, 2004 [Inventor—Ziegerson; Applicant—PR Pharmaceuticals] [3 pages].
Final Office Action issued on Nov. 2, 2012 for U.S. Appl. No. 10/553,003, filed Aug. 15, 2006 [Inventor—Zeigerson; Applicant—PR Pharmaceuticals, Inc.] [9 pages].
Response to Non-Final Office Action filed on Oct. 12, 2012 for U.S. Appl. No. 10/553,003, filed Aug. 15, 2006 [Inventor—Zeigerson; Applicant—PR Pharmaceuticals, Inc.] [9 pages].
Non-Final Office Action issued on Apr. 10, 2012 for U.S. Appl. No. 10/553,003, filed Aug. 15, 2006 [Inventor—Zeigerson; Applicant—PR Pharmaceuticals, Inc.] [14 pages].
Response to Non-Final Office Action filed on Jan. 4, 2013 for U.S. Appl. No. 11/799,700, filed May 1, 2007 [Inventor—Zeigerson; Applicant—PR Pharmaceuticals, Inc.] [5 pages].
Non-Final Office Action issued on Oct. 4, 2012 for U.S. Appl. No. 11/799,700, filed May 1, 2007 [Inventor—Zeigerson; Applicant—PR Pharmaceuticals, Inc.] [18 pages].
Office Action issued on Nov. 23, 2012 for CA Pat. App. No. 2,533,592, which is a national phase of Intl. App. No. PCT/US2004/022817, filed on Jul. 15, 2004 [Inventor—Cook; Applicant—PR Pharmaceuticals] [4 pages].
Response to Office Action filed on Aug. 31, 2012 for CA Pat. App. No. 2,533,592, which is a national phase of Intl. App. No. PCT/US2004/022817, filed on Jul. 15, 2004 [Inventor—Cook; Applicant—PR Pharmaceuticals] [15 pages].
Office Action issued on Mar. 1, 2012 for CA Pat. App. No. 2,533,592, which is a national phase of Intl. Pat. App. No. PCT/US2004/022817, filed on Jul. 15, 2004 [Inventor—Cook; Applicant—PR Pharmaceuticals] [3 pages].
Office Action issued on Jan. 30, 2013 for EP Pat. App. No. 04778361.8, which is a national phase of Intl. Pat. App. No. PCT/US2004/022817, filed on Jul. 15, 2004 [Inventor—Cook; Applicant—PR Phramaceuticas] [6 pages].
Reply to Communication from Examining Division filed on Nov. 8, 2011 for EP Pat. Appl. No. 04778361.8, which is a national phase of Intl. Pat. App. No. PCT/US2004/022817, filed on Jul. 15, 2004 [Inventor—Cook; Applicant—PR Pharmaceuticals] [7 pages].
Communication from the Examining Divison issued on Jan. 29, 2013 for EP Pat. App. No. 11187401.2, which is a divisional of EP 04778361.8, national phase of Intl. Pat. App. No. PCT/US2004/022817, filed on Jul. 15, 2004 [Inventor—Cook; Applicant—PR Pharmaceuticals] [6 pages].
Amendment filed on Oct. 25, 2012 for EP Pat. App. No. 11187401.2, which is a divisional of EP 04778361.8, national phase of Intl. Pat. App. No. PCT/US2004/022817, filed on Jul. 15, 2004 [Inventor—Cook; Applicant—PR Pharmaceuticals] [6 pages].
Extended European Search Report issued on Mar. 28, 2012 for EP Pat. App. No. 11187401.2, which is a divisional of EP 04778361.8, national phase of Intl. Pat. App. No. PCT/US2004/022817, filed on Jul. 15, 2004 [Inventor—Cook; Applicant—PR Pharmaceuticals] [9 pages].
Response to Office Action filed on Oct. 10, 2012 for CA Pat. App. No. 2,532,302, which is a national phase of Intl. Pat. App. No. PCT/US2004/022816, filed on Jul. 15, 2004 [Inventor—Cook; Applicant—PR Pharmaceuticals] [11 pages].
Office Action issued on Apr. 10, 2012 for CA Pat. App. No. 2,532,302, which is a national phase of Intl. Pat. App. No. PCT/US2004/022816, filed on Jul. 15, 2004 [Inventor—Cook; Applicant—PR Pharmaceuticals] [2 pages].
Decision of Rejection issued on Aug. 3, 2012 for CN Pat. App. No. 200480026606.7, which is a national phase of Intl. Pat. App. No. PCT/US2004/022816, filed on Jul. 15, 2004 [Inventor—Cook; Applicant—PR Pharmaceuticals] [6 pages].
Office Action issued on Jan. 30, 2013 for EP Pat. App. No. 04778360.0, which is a national phase of Intl. Pat. App. No. PCT/US2004/002816, filed on Jul. 15, 2004 [Inventor—Cook; Applicant—PR Pharmaceuticals] [6 pages].
Reply to Communication filed on Nov. 8, 2011 for EP Pat. App. No. 04778360.0, which is a national phase of Intl. Pat. App. No. PCT/US2004/022816, filed on Jul. 15, 2004 [Inventor—Cook; Applicant—PR Pharmaceuticals] [14 pages].
Extended European Search Report and Opinion issued on May 14, 2012 for EP Pat. App. No. 11187402.0, which is a divisional of EP 04778360.0, national phase of Intl. Pat. App. No. PCT/US2004/022816, filed on Jul. 15, 2004 [Inventor—Cook; Applicant—PR Pharmaceuticals] [9 pages].
Office Action issued on Dec. 16, 2011 for JP Pat. App. No. 2006-520347, which is a national phase of Intl. Pat. App. No. PCT/US2004/022816, filed on Jul. 15, 2004 [Inventor—Cook; Applicant—PR Pharmaceuticals] [3 pages].
Non-Final Office Action issued on Apr. 26, 2013 for U.S. Appl. No. 10/564,494, filed Jun. 27, 2006 [Inventor—Cook; Applicant—PR Pharmaceuticals] [17 pages].
Final Office Action issued on May 6, 2013 for U.S. Appl. No. 11/799,700, filed May 1, 2007 [Inventor—Ziergerson; Applicant—PR Pharmaceuticals] [21 pages].

* cited by examiner

CONTROLLED RELEASE COMPOSITIONS

CROSS REFERENCE TO RELATED APPLICATIONS

This application is a national phase application filed under 35 U.S.C. §371 of PCT Application Number PCT/US2004/022817, filed Jul. 15, 2004, which claims priority from U.S. Provisional Patent Application No. 60/489,402, filed Jul. 23, 2003.

FIELD OF THE INVENTION

The present invention relates to controlled release compositions including a water soluble bioactive agent, an organic ion and a polymer, wherein the content of said bioactive agent is about two to four fold higher than in the absence of organic ion.

BACKGROUND OF THE INVENTION

Currently there are numerous controlled release formulations on the market that contain various bioactive agents, such as GnRH analogs, human growth hormone, risperidone, and somatostatin analogs of which octreotide acetate is an example. Such formulations are preferred by physicians and veterinarians and by their patients because they reduce the need for multiple injections. Unfortunately, there are many problems with the formulations for controlled release compositions such as the fact that many popular bioactive agents are not good candidates for controlled release compositions due to their substantial water solubility. The use of highly soluble bioactive agents may result in low drug content and an undesirable "burst" of bioactive agent upon contact with an aqueous solution, such as by administration to a patient or introduction to a physiological medium, which often limits the useable content of bioactive agent achievable in practice.

Various methods of solving the water solubility problem have been devised with some success. One such effort is disclosed in U.S. Pat. No. 5,776,885 by Orsolini et al. Orsolini converted water soluble peptides to their water insoluble addition salts with pamoic, tannic or stearic acid prior to their encapsulation in sustained release compositions. Encapsulation within a polymer matrix is then performed by dispersing the water insoluble peptide in a polymer solution and forming controlled release compositions via either extrusion or a cumbersome coacervation method. One disadvantage of this approach is the requirement to obtain the water insoluble addition salt prior to encapsulation within a polymer matrix. Furthermore, it was discovered in the present work that when pre-formed addition salts were employed in an emulsion process to form microparticles the result was release of substantial amounts of modified or degraded peptide from the composition when placed in an aqueous physiological buffer. Modification was in the form of undesirable acylation of bioactive agent.

Controlled release compositions with a high drug load, low burst effect upon administration, and minimum degradation of the bioactive agent are greatly needed to realize the benefits of these types of compositions as human or veterinary therapeutics.

SUMMARY OF THE INVENTION

It has now been discovered that controlled release compositions capable of administration in a concentrated, low dose volume form which release active agent for a prolonged period of time can originate from water soluble bioactive agents without first converting them to a water insoluble form. This finding is in direct contrast to previous work in this field that suggested that water soluble bioactive agents would need to be manipulated in some way, for example to render them water insoluble, prior to forming a sustained release composition. Additionally, the conversion process required in previous compositions, resulted in a high percentage of degradation of the bioactive agent, whereas the compositions of the present invention are prepared with an understanding of how to reduce degradation. The presence of the bioactive agent in a physiologically relevant form creates an increased core load with regard to previously prepared compositions, which are susceptible to significant degradation. Reduced degradation translates into increased release of unmodified bioactive agent, thus allowing for a smaller injection volume to deliver the same dose of bioactive agent. The compositions of the present invention offer a vast improvement over previous inventions in that they provide a way to deliver a relatively undegraded bioactive agent over a prolonged period of time using a reduced dose volume.

In one embodiment, the controlled release compositions are microparticles and nanoparticles. In a particular embodiment, the microparticles and nanoparticles are biodegradable. In another particular embodiment, the polymer is selected from the group consisting of, but not limited to, poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and polyorthoester, biodegradable polyurethanes, blends and copolymers thereof.

In another embodiment, the bioactive agent is selected from the group consisting of, but not limited to, proteins, nucleic acids, carbohydrates, peptides, small molecule pharmaceutical substances, immunogens, metabolic precursors capable of promoting growth and survival of cells and tissues, antineoplastic agents, hormones, antihistamines, cardiovascular agents, anti-ulcer agents, bronchodilators, vasodilators, central nervous system agents, narcotic antagonists and the like.

In a certain embodiment, the organic ion is selected from the group consisting of anionic and cationic materials. In a particular embodiment, the organic ion is selected from pamoate, trifluoromethyl-p-toluate, cholate, 2-naphthalene sulfonate, 2,3-naphthalene dicarboxylate, 1-hydroxy-2-naphthoate, 3-hydroxy-2-naphthoate, 2-naphthoate and salicylsalicylate.

In another embodiment, degradation includes acylation of the bioactive agent or lysis of the polymer. In a particular embodiment the acylation reaction involves nucleophilic attack of an amino group of a bioactive agent directed to a carbonyl carbon of a polyester such as poly(d,l-lactide-co-glycolide). It is hypothesized that degradation of the bioactive agent is prevented or reduced in the present compositions by facilitated protonation of potential nucleophiles (e.g., amino groups), thus rendering the nucleophiles less apt to participate in acylation reactions with the PLGA polymer backbone or fragments thereof.

In another embodiment, the molar stoichiometry of the bioactive agent relative to the organic ion ranges from about 0.5 to 2.0. In a particular embodiment the molar stoichiometry of the bioactive agent relative to the organic ion ranges from about 1.0 to 1.5.

In another certain embodiment, the present invention provides a controlled release composition including a polymer and a bioactive agent in the form of a complex with an organic ion. Such a complex may be formed when an organic ion and a bioactive agent form a close physical association.

In another embodiment the bioactive agent content may be increased relative to the bioactive agent content of compositions prepared by the method of the present invention in the absence of an organic ion.

In a particular embodiment, the bioactive agent is octreotide acetate and the organic ion is pamoate. In another particular embodiment, the bioactive agent is water soluble.

In another embodiment the bioactive agent content may be increased relative to the bioactive agent content of previously prepared compositions.

In another embodiment the core load of present compositions is greater than about 9% and/or the percentage of degraded product is about 25% or less.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention as claimed.

DESCRIPTION OF ILLUSTRATIVE EMBODIMENTS

Definitions

For the purposes of the present invention, the following terms shall have the following meanings:

For the purposes of the present invention, the term "biodegradable" refers to polymers that dissolve or degrade in vivo within a period of time that is acceptable in a particular therapeutic situation. Such dissolved or degraded product may include a smaller chemical species. Degradation can result, for example, by enzymatic, chemical and/or physical processes. Biodegradation takes typically less than five years and usually less than one year after exposure to a physiological pH and temperature, such as a pH ranging from 6 to 9 and a temperature ranging from 22 C. to 38 C.

For the purposes of the present invention, the term "organic phase" refers to the solution of solvent, polymer and bioactive agent created in the methods of the present invention that will then be contacted with an aqueous phase in order to create the controlled release compositions of the present invention.

For the purposes of the present invention, the term "degradation" refers to any unwanted modification to the bioactive agent, such as acylation, or modification of the polymer such as lysis.

For the purposes of the present invention, the term "aqueous phase" refers to the solution of water and organic ion agent created in the methods of the present invention that will then be contacted with an organic phase in order to create the controlled release compositions of the present invention.

For the purposes of the present invention, the term "combining" refers to any method of putting two or more materials together. Such methods include, but are not limited to, mixing, blending, commingling, concocting, homogenizing, incorporating, intermingling, fusing, joining, shuffling, stirring, coalescing, integrating, confounding, joining, uniting, and the like.

For the purposes of the present invention, ranges may be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

For the purposes of the present invention, the term "bioactive agent" refers to any agent with biological activity either in vivo or in vitro, where biological activity may be detected as an observable change in overall health or at least one health marker (i.e., symptom) of an individual, as a change in a relevant surrogate biological marker or as a change in the chemical structure or conformation of a physiologically relevant molecule.

For the purposes of the present invention, the term "organic ion" refers to a cationic or anionic material. Organic ions may be present in their salt or acid forms. Exemplary organic ions include pamoate, naphthoate, cholate and the like.

For the purposes of the present invention, a "controlled release composition" shall refer to any formulation with a different release profile than native bioactive agent. Typically release profiles will include physiologically detectable concentrations of a bioactive agent over a period of at least one week, at least one month, at least 45 days, or for longer than 45 days.

Moreover, for the purposes of the present invention, the term "a" or "an" entity refers to one or more of that entity; for example, "a protein" or "an peptide" refers to one or more of those compounds or at least one compound. As such, the terms "a" or "an", "one or more" and "at least one" can be used interchangeably herein. It is also to be noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated or biologically pure bioactive agent is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

Reference will now be made in detail to certain embodiments of the invention, examples of which are illustrated in the accompanying Examples section.

Controlled release compositions of the present invention include the following disclosed components. These and other materials are disclosed herein, and it is understood that when combinations, subsets, interactions, groups, etc. of these materials are disclosed that while specific reference of each various individual and collective permutation of these compounds may not be explicitly disclosed, each is specifically contemplated and described herein. For example, if a number of bioactive agents are disclosed and discussed and a number of modifications that can be made to a number of molecules including bioactive agents are discussed, specifically contemplated is each and every combination and permutation of bioactive agent and the modifications that are possible unless specifically indicated to the contrary. Thus, if a class of molecules A, B, and C are disclosed as well as a class of molecules D, E, and F and an example of a combination molecule, A-D is disclosed, then even if it is not individually recited each is individually and collectively contemplated meaning combinations, A-E, A-F, B-D, B-E, B-F, C-D, C-E and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the present invention.

Bioactive Agents

In one embodiment of the present invention, the bioactive agent is selected from the group consisting of a protein, a nucleic acid, a carbohydrate, a peptide or a small molecule pharmaceutical substance. Proteins of use in the present invention include but are not limited to antibodies, therapeutic proteins, human growth hormone, interferon alpha, interferon beta, interferon gamma, insulin, calcitonin, interleukin-1, interleukin-2, and the like. Nucleic acids of use in the present invention include DNA, RNA, chemically modified DNA and chemically modified RNA, aptamers, antisense, RNA interference, and small RNA interference. Carbohydrates include heparin, low molecular weight heparin and the like. Peptides include LHRH agonists and synthetic analogs thereof, somatostatin and synthetic analogs thereof, hormones, octreotide, glucagon-like peptide, oxytocin and the like. Small molecule pharmaceutical substances include, but are not limited to, antiinfectives, cytotoxics, antihypertensives, antifungal agents, antipsychotics, antidiabetic agents, immune stimulants, immune suppressants, antibiotics, antivirals, anticonvulsants, antihistamines, cardiovascular agents, anticoagulants, hormones, antimalarials, analgesics, anesthetics, steroids, nonsteroidal anti-inflammatories, antiemetics.

In another embodiment, the bioactive agent is an immunogen. Such immunogen may be selected from the group consisting of, but not limited to, immunogens for stimulating antibodies against hepatitis, influenza, measles, rubella, tetanus, polio, rabies, and the like.

In another embodiment, the bioactive agent is a substance or metabolic precursor capable of promoting growth and survival of cells and tissues or augmenting the functioning of cells. Such substance or metabolic precursor may be selected from the group consisting of, but not limited to, a nerve growth promoting substance such as a ganglioside, a nerve growth factor, and the like; a hard or soft tissue growth promoting agent such as fibronectin, human growth hormone, a colony stimulating factor, bone morphogenic protein, platelet-derived growth factor, insulin-derived growth factors, transforming growth factor-alpha, transforming growth factor-beta, epidermal growth factor, fibroblast growth factor, interleukin-1, vascular endothelial growth factor, keratinocyte growth factor, dried bone material, and the like.

In another embodiment, the bioactive agent is an antineoplastic agent. In a particular embodiment, the antineoplastic agent is selected from the group consisting of, but not limited to, methotrexate, 5-fluorouracil, adriamycin, vinblastin, cisplatin, tumor-specific antibodies conjugated to toxins, tumor necrosis factor, and the like.

In other embodiments, the bioactive agent is selected from the group consisting of, but not limited to, antihistamines such as diphenhydramine, and the like; cardiovascular agents such as papverine, fibrinolytics such as streptokinase and the like; anti-ulcer agents such as isopropamide iodide, and the like; bronchodilators such as metaproternal sulfate, aminophylline, and the like; vasodilators such as theophylline, niacin, minoxidil, and the like; central nervous system agents such as tranquilizers, β-adrenergic blocking agents, dopamine, and the like; antipsychotic agents such as risperidone, narcotic antagonists such as naltrexone, naloxone, buprenorphine; and other like substances.

In a certain embodiment, the bioactive agent is capable of providing a local or systemic biological, physiological or therapeutic effect in the biological system in which it is applied. For example, the agent may act to control infection or inflammation, enhance cell growth and tissue regeneration, control tumor growth and enhance bone growth, among other functions.

In another embodiment, controlled release compositions may contain combinations of two or more bioactive agents. In a particular embodiment, controlled release compositions contain five or fewer bioactive agents. In another particular embodiment, controlled release compositions contain one bioactive agent.

In another embodiment, a "pharmaceutical equivalent" of a bioactive agent is any compound with similar or greater in vitro activity to the bioactive agent itself. In a particular example, a pharmaceutical equivalent has a similar chemical structure to the bioactive agent, contains only the biologically active portion of the bioactive agent or is a synthetic analog of the bioactive agent.

In another embodiment, bioactive agents of the present invention may include various salt forms and derivatives including covalent linkages to hydrophilic polymers such as poly(ethylene glycol) and poly(propylene glycol).

In a particular embodiment, the bioactive agent has the potential to exhibit at least one positive or negative charge or both positive and negative charge.

In a particular embodiment, the bioactive agent is water soluble.

In another particular embodiment, the bioactive agent is solubilized in an organic solvent, optionally including a cosolvent. The bioactive agent may be soluble in water or in organic solvents or both.

It will be appreciated by one skilled in the art that the actual amounts of bioactive agents to utilize in a particular case will vary according to the specific compound being utilized, the particular compositions formulated, the mode of application, and the particular situs and patient being treated. Dosages for a given host can be determined using conventional considerations, for example, by customary comparison of the differential activities of the subject compounds and of a known bioactive agent, for example, by means of an appropriate conventional pharmacological protocol. Physicians and formulators, skilled in the art of determining doses of pharmaceutical compounds, will have no problems determining dose according to standard recommendations.

Organic Ion

Organic ions of use in the present invention include anionic and cationic materials. Anionic materials include, but are not limited to, the following organic acids and their salts: pamoic, dodecylsulfuric, cholic, trifluoromethyl-p-toluic, 2-naphthalene sulfonic, 2,3-naphthalene dicarboxylic, 1-hydroxy-2-naphthoic, 3-hydroxy-2-naphthoic, 2-naphthoic, and salicylsalicylic. Salt forms of the anionic materials may include, sodium, ammonium, magnesium, calcium and the like.

Cationic molecules include, but are not limited to, those having an ammonium or guanidinium group or a substituted ammonium group. Organic anionic agents are used with bioactive agents that have one or more functional groups having, or capable of adopting, a positive charge, such as an ammonium or guanidinium group. Organic cationic agents can be used with bioactive agents that have one or more functional groups having or capable of adopting a negative charge such as a carboxyl, sulfate, sulfonate, phosphate, or phosphonate group.

Organic ion agents of use in the present invention may be soluble in water and in the organic phase to the extent required to enhance drug loading and encapsulation efficiency. In a particular embodiment, concentration of the organic ion agent in the aqueous phase ranges from about 0.5 to 100 mM. In another particular embodiment, the concentration of the organic ion ranges from about 5 to 50 mM.

Biodegradable Microparticles

In certain embodiments, the controlled release composition is a microparticle.

In certain embodiments, a bioactive agent is associated with a biodegradable polymer in a microparticle form. In a particular embodiment, a microparticle has a diameter less than 1.0 mm and typically between 1.0 and 200.0 microns. Microparticles include both microspheres and microcapsules, and may be approximately spherical or have other geometries. Microspheres are typically approximately homogeneous in composition and microcapsules comprise a core of a composition distinct from a surrounding shell. For purposes of this disclosure, the terms microsphere, microparticle and microcapsule are used interchangeably.

In certain embodiments, microparticles can be made with a variety of biodegradable polymers. Suitable biocompatible, biodegradable polymers include, for example, poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and poly(lactide)s or poly(lactide-co-glycolide)s, biodegradable polyurethanes, blends and copolymers thereof.

In a particular embodiment, the microparticle is made of poly(d,l-lactide-co-glycolide) (PLGA). PLGA degrades when exposed to physiological pH and hydrolyzes to form lactic acid and glycolic acid, which are normal byproducts of cellular metabolism. The disintegration rate of PLGA polymers will vary depending on the polymer molecular weight, ratio of lactide to glycolide monomers in the polymer chain, and stereoregularity of the monomer subunits. Mixtures of L and D stereoisomers that disrupt the polymer crystallinity will increase polymer disintegration rates. In addition, microspheres may contain blends of two or more biodegradable polymers, of different molecular weight and/or monomer ratio.

In other alternative embodiments, derivatized biodegradable polymers, including hydrophilic polymers attached to PLGA, can be used to form microspheres. In particular embodiments, the hydrophilic polymer is selected from the group consisting of, but not limited to, poly(ethylene glycol), poly(propylene glycol) and copolymers of poly(ethylene glycol) and poly(propylene glycol).

Biodegradable Nanoparticles

In certain embodiments, the controlled release composition is a nanoparticle.

In certain embodiments, the bioactive agent, with or without a hydrophilic polymer attached, is associated with biodegradable submicron particles for controlled release of the bioactive agent. A nanoparticle has a diameter ranging from 20.0 nanometers to about 2.0 microns and is typically between 100.0 nanometers and 1.0 micron.

Nanoparticles can be created in the same manner as microparticles, except that high-speed mixing or homogenization is used to reduce the size of the polymer/bioactive agent emulsions to less than 2.0 microns and typically below 1.0 micron. Alternative methods for nanoparticle production are known in the art and may be employed for the present invention.

Production of Controlled Release Compositions

Controlled release compositions of the present invention may be made by any emulsion process known in the art.

In one embodiment an organic phase, containing one or more solvents, a bioactive agent and a polymer, is contacted with an aqueous phase, containing an organic ion. In a particular embodiment, the organic phase additionally includes a cosolvent. In another particular embodiment, the aqueous phase additionally includes an emulsifying agent.

In a particular embodiment, the organic phase is contacted with the aqueous phase to form an emulsion wherein the emulsion comprises droplets of the organic phase dispersed in the aqueous phase. Solvent is subsequently removed from the emulsion droplets to form hardened microparticles. The hardened microparticles may then be recovered from the aqueous phase and dried.

In one embodiment, the organic phase may contain solvents including but not limited to, methylene chloride, ethyl acetate, benzyl alcohol, acetone, acetic acid, propylene carbonate and other solvents in which the biodegradable polymer is soluble. In a particular embodiment, the solvent of the organic phase may be selected from the group consisting of ethyl acetate and methylene chloride.

In one embodiment, the aqueous phase may contain solvents including but not limited to, methanol, benzyl alcohol, isopropyl alcohol, water, dimethylsulfoxide, N,N-dimethylformamide, methylene chloride and other solvents in which the bioactive agent is soluble.

In another embodiment, cosolvents may be added to the organic phase. They are optionally used to promote solubility of the bioactive agent in the organic phase. In a particular embodiment, they are selected from the group consisting of, but not limited to, methyl alcohol, ethyl alcohol, isopropyl alcohol, N-methyl pyrrolidinone, dimethyl sulfoxide, N,N-dimethyl formamide, $PEG_{200}$, $PEG_{400}$ and benzyl alcohol. In another particular embodiment, the cosolvent may be present between about 0 and 90% w/w of the solvent of the organic phase. In another particular embodiment, the cosolvent is present between about 0 and 50% w/w of the solvent of the organic phase. The bioactive agent may be dissolved first in an appropriate volume of the cosolvent which is then added to the solvent of the organic phase, preferably having the biodegradable polymer dissolved therein, so as to form a solution of all the components of the organic phase. A person of ordinary skill can adjust the volumes and order of addition to achieve the desired solution of bioactive agent and biodegradable polymer. In a certain embodiment, the bioactive agent will be present in the organic phase at a concentration of about 1-20% w/w. In a particular embodiment, the biodegradable polymer will be present in the organic phase at a concentration of about 240% w/w. In another particular embodiment, the biodegradable polymer will be present in the organic phase at a concentration of about 5-20% w/w.

Organic ions are dissolved in the aqueous phase. In a certain embodiment, they are dissolved at a concentration of between about 0.1 and 1000 mM. In a particular embodiment, they are dissolved at a concentration of between about 1 to 100 mM. The concentration may be adjusted for each particular organic ion agent and bioactive agent to achieve the desired drug loading and encapsulation efficiency.

One or more emulsifying agents may be added to the aqueous phase to stabilize the emulsion. Emulsifying agents may be selected from the group consisting of, but not limited to, poly(vinyl alcohol), albumin, lecithin, vitamin E TPGS and polysorbates. The emulsifying agents are present at a concentration in the aqueous phase between 0 and 10% (w/w). In a particular embodiment, they are present at a concentration between 0.5 to 5% w/w.

Pharmaceutical Formulations

In addition to the compounds formulated for parenteral administration, such as intravenous or intramuscular injection, other alternative methods of administration of the present invention may also be used, including but not limited to intradermal administration, pulmonary administration, buccal administration, transdermal and transmucosal administration. Transmucosal administration may include, but is not limited to, ophthalmic, vaginal, rectal and intranasal. All such methods of administration are well known in the art.

In a particular embodiment, the controlled release composition of the present invention may be administered intranasally, such as with nasal solutions or sprays, aerosols or inhalants. Nasal solutions are usually aqueous solutions designed to be administered to the nasal passages in drops or sprays. Nasal solutions are prepared so that they are similar in many respects to nasal secretions. Thus, the aqueous nasal solutions usually are isotonic and slightly buffered to maintain a pH of 5.5 to 6.5.

Antimicrobial preservatives, similar to those used in ophthalmic preparations, and appropriate drug stabilizers, if required, may be included in any of the formulations. Preservatives and other additives may be selected from the group consisting of, but not limited to, antimicrobials, anti-oxidants, chelating agents, inert gases and the like. Various commercial nasal preparations are known and include, for example, antibiotics and antihistamines and are used for asthma prophylaxis.

In another embodiment, controlled release compositions of the present invention are applied topically. Such controlled release compositions include, but are not limited to, lotions, ointments, creams, gels, drops, suppositories, sprays, liquids and powders. Conventional pharmaceutical carriers, aqueous, powder or oily bases, thickeners and the like may be necessary or desirable.

Excipients, Carriers and Diluents

Controlled release compositions of the present invention can be formulated in any excipient the biological system or entity can tolerate. Examples of such excipients include water, saline, Ringer's solution, dextrose solution, Hank's solution and other aqueous physiologically balanced salt solutions. Nonaqueous vehicles, such as fixed oils, polyethylene glycol and injectable organic esters such as ethyl oleate may also be used. Other useful formulations include suspensions containing viscosity-enhancing agents, such as sodium carboxymethylcellulose, sorbitol or dextran.

Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol.

Pharmaceutical carriers for controlled release compositions of the present invention are known to those skilled in the art. Those most typically utilized are likely to be standard carriers for administration to humans including solutions such as sterile water, saline and buffered solutions at physiological pH.

The controlled release compositions of the present invention may be suspended in any aqueous solution or other diluent for injection in a human or animal patient in need of treatment. Aqueous diluent solutions may further include a viscosity enhancer selected from the group consisting of sodium carboxymethylcellulose, sucrose, mannitol, dextrose, trehalose and other biocompatible viscosity enhancing agents. The viscosity may be adjusted to a value between 2 centipoise (cp) and 100 cp, preferably between 4 and 40 cp.

In a particular embodiment, a surfactant may be included in the diluent to enhance suspendability of the controlled release composition. Surfactants may be selected from the group consisting of, but not limited to, polysorbates and other biocompatible surfactants. Surfactants are used at a concentration of between 0 and 5% (w/w), preferably between 0.1 and 1% w/w.

EXAMPLES

The following examples are included to demonstrate particular embodiments of the invention. It should be appreciated by those of skill in the art that the techniques disclosed in the examples which follow represent techniques discovered by the inventors to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Example 1

Conventional Preparation of Octreotide Acetate Encapsulated in Poly(lactide-co-glycolide) (PLGA) Microparticles Using Co-Solvents According to Previously Used Methods.

Octreotide acetate microparticle formulations were prepared to investigate the effect of different co-solvents in the organic phase. Formulations A-F, prepared using an oil-in-water emulsion/solvent extraction technique, are summarized in Table 1. PLGA polymer (50:50 lactide/glycolide, MW 24,000, 180 mg) was dissolved in ethyl acetate (EtOAc, 900 μL), and octreotide acetate (20 mg) dissolved in a co-solvent (Table 1) was added to the polymer solution. The resulting homogeneous organic phase was added to an aqueous phase (2 mL) containing 1% poly(vinyl alcohol) (PVA) and the mixture was vortexed for 15-30 seconds. The emulsion was poured into a solvent extraction solution (10 mM sodium phosphate, pH 8.0, 150 mL) and stirred for four hours to extract EtOAc. Particles were isolated by filtration, washed with water and air dried overnight. The formulations were characterized by particle size, scanning electron microscopy (SEM), morphology, octreotide core load and in vitro release profiles.

Formulation D was repeated using an emulsifying device, such as that disclosed in PCT Application Serial No. PCT/US04/11485, that combined a homogeneous organic phase (2 mL) consisting of octreotide acetate (20 mg), MeOH (100 μL), PLGA polymer (50:50 lactide/glycolide, MW 24,000, 180 mg) and EtOAc (1.9 mL) with a 1% PVA aqueous phase (4 mL). The emulsion was then added to a solvent extraction solution and stirred for four hours to extract EtOAc. This process produced formulation D2 (Table 1).

The co-solvents investigated had a small influence on particle size and core load. Particle sizes were larger with the higher viscosity poly(ethylene glycol) (PEG) co-solvents. In contrast, core loads were similar for the methanol (MeOH) and PEG co-solvents (formulations A-C). The highest core loads were obtained for the MeOH cosolvent with a pH 8 buffered emulsion step (formulation D2) and for the dimethyl sulfoxide (DMSO) cosolvent (formulation F).

In vitro release kinetics were measured in either phosphate buffered saline (PBS, pH 7.2, 37° C.) or 100 mM sodium acetate (NaOAc, pH 4.0, 37° C.). An example is shown in Table 2 (Formulation D2). The PEG co-solvent systems showed the highest initial peptide burst (8-10%), while the remaining formulations had an initial burst in the range of 2-3%. All the formulations released peptide for at least 6 weeks. There was a decrease in the relative release rates for formulations prepared with polar aprotic solvents (formulations E-F) resulting in lower total release of peptide relative to the other formulations.

Octreotide acetate as the free peptide was measured to be 95% intact by high-pressure liquid chromatography (HPLC) following incubation in the release medium (PBS, pH 7.2, 37° C.) after 49 days. In contrast, incubation of octreotide acetate PLGA microparticle formulations produced 55% of modified peptide species after 70 days in the release medium (PBS, pH 7.2, 37° C., Table 2). HPLC analysis showed that the new peptide entities were more hydrophobic than native octreotide acetate. HPLC/MS analysis revealed masses consistent with acylation of the parent peptide by PLGA polymer. The masses found were consistent with random acylation, for example, peptide plus one or two glycolic or lactic acid monomers in any combination. It may be that acylation products arise from attack on PLGA fragments or the polymer backbone by nucleophilic moieties in octreotide. At a lower pH these moieties likely would be protonated reducing their nucleophilicity and consequently the amount of acylated product. It was observed that formation of acylated byproducts for octreotide acetate PLGA microparticles incubated in 100 mM sodium acetate (NaOAc, pH 4.0) buffer was reduced to 1.25% at 49 days, in marked contrast to the results for PBS buffer (55%).

TABLE 1

Octreotide Acetate Encapsulation in PLGA Microparticles.

| | Co-solvent in organic phase | Composition of Aqueous Phase | Median particle size | Core load (encaps. eff.) | Burst (%) | Total Peptide Release (Acylated) |
|---|---|---|---|---|---|---|
| A | PEG$_{200}$ (100 μL) | 1% PVA | 49 μm | 2.83% (28%) | 7.96 | 72.6% (44%) |
| B | PEG$_{400}$ (100 μL) | 1% PVA | 76 μm | 3.20% (32%) | 10.4 | 63.0% (48%) |
| C | MeOH (50 μL) | 1% PVA | 25 μm | 2.75% (28%) | 2.91 | 65.7% (50%) |
| D | MeOH (100 μL) | 1% PVA + 10 mM PO$_4$ (pH8) | 34 μm | 5.57% (56%) | 2.58 | 65.1% (50%) |
| D2 | MeOH (100 μL) | 1% PVA + 10 mM PO$_4$ (pH8) | 60 μm | 5.66% (57%) | 1.90 | 85.8% (55%) |
| E | DMF (100 μL) | 1% PVA | 38 μm | 3.41% (34%) | 1.97 | 50.3% (33%) |
| F | DMSO (100 μL) | 1% PVA | 38 μm | 4.88% (49%) | 2.74 | 43.4% (36%) |

TABLE 2

Formulation D2
100 mM NaOAc (pH 4)

| Day | % Peptide Released | % Acylated Peptide Released |
|---|---|---|
| 0 | 0.0 | 0.0 |
| 1 | 5.55 | 0.15 |
| 3 | 13.75 | 0.78 |
| 6 | 53.47 | 4.11 |
| 10 | 71.74 | 5.16 |
| 14 | 72.19 | 5.26 |
| 20 | 72.21 | 5.28 |
| 24 | 72.22 | 5.30 |
| 29 | 72.22 | 5.30 |
| 34 | 72.22 | 5.30 |
| 42 | 72.22 | 5.30 |
| 48 | 72.22 | 5.30 |

Formulation D2
PBS (pH 7)

| Day | % Peptide Released | % Acylated Peptide Released |
|---|---|---|
| 0 | 0.0 | 0.0 |
| 1 | 1.81 | 0.08 |
| 3 | 3.09 | 0.22 |
| 6 | 4.87 | 0.59 |
| 10 | 7.54 | 1.98 |
| 14 | 10.42 | 4.29 |
| 20 | 17.81 | 10.51 |
| 24 | 20.69 | 14.06 |
| 29 | 23.86 | 18.86 |
| 34 | 26.21 | 23.12 |
| 42 | 32.91 | 28.73 |
| 48 | 35.13 | 32.14 |
| 57 | 36.50 | 35.10 |
| 64 | 37.83 | 37.41 |
| 71 | 38.42 | 45.82 |
| 78 | 38.58 | 46.37 |
| 85 | 38.64 | 46.70 |

Formulation AG
PBS (pH 7)

| Day | % Peptide Released | % Acylated Peptide Released |
|---|---|---|
| 0 | 0.0 | 0.0 |
| 1 | 8.04 | 0.33 |
| 2 | 9.09 | 0.47 |
| 6 | 12.27 | 0.65 |
| 15 | 17.75 | 1.23 |
| 24 | 20.03 | 1.78 |
| 29 | 23.78 | 2.66 |
| 35 | 36.16 | 5.62 |
| 42 | 43.80 | 8.15 |
| 49 | 51.17 | 11.13 |
| 57 | 61.47 | 15.57 |
| 64 | 67.63 | 18.16 |

Example 2

Production of Water Insoluble Organic Acid Salts (Complexes) of Octreotide and Encapsulation in PLGA Microparticles According to Previously Used Methods.

Organic ion agents were investigated where the organic ion was initially complexed with octreotide acetate to form a water insoluble salt followed by encapsulation in PLGA microparticles.

Sodium Dodecylsulfate (SDS).

An octreotide-SDS complex was prepared by dissolving octreotide acetate (100 mg) in H$_2$O (500 μL). SDS (1.5 equiv, 43.2 mg) dissolved in H$_2$O (500 μL) was added drop wise to the octreotide acetate solution with vortexing at room temperature. A precipitate immediately formed. The sample was centrifuged at 10,000 rpm for 1 minute and the supernatant removed by pipette. The precipitate was washed with cold water and lyophilized providing an octreotide-SDS complex (95.3 mg). RP-HPLC analysis showed a pronounced broadening of the octreotide peak indicating formation of the octreotide/SDS complex. Formulations G-I were prepared using an oil-in-water emulsion/solvent extraction technique. PLGA polymer (MW 24,000, 180 mg) was dissolved in EtOAc (900 µL). Octreotide/SDS complex was dissolved in MeOH (100 µL) and added to the polymer solution. This resulted in a heterogeneous organic phase. In the case of formulation I (Table 3) an additional aliquot of MeOH (100 µL) was added to produce a homogeneous organic phase. The resulting organic phase was added to an aqueous phase (2 mL) containing 1% PVA and the mixture was vortexed for 15-30 seconds. The emulsion was poured into a solvent extraction solution (10 mM sodium phosphate, pH 8.0, 150 mL) and stirred for four hours to extract EtOAc. Particles were isolated by filtration, washed with water and air dried overnight. The formulations were characterized by particle size, SEM morphology, octreotide core load and in vitro release profiles.

The measured core load for formulations G-I prepared from the octreotide-SDS complex were relatively low, between 0.6-2.6% (Table 3). Also the median particle size was reduced by approximately 40% relative to formulations (A-F) prepared with octreotide acetate.

The in vitro release profiles of formulations G-I in PBS were quite similar. Each had an initial burst of approximately 20% followed by three weeks of 1.5% release/week. After three weeks the rate of release increased to approximately 7.0% release/week, culminating in approximately 80% total peptide release at 9 weeks.

The in vitro PBS release assay with these formulations resulted in the release of similar amounts of acylated (40-55%) and total peptide compared to octreotide acetate (formulations A-F).

TABLE 3

Octreotide-SDS Complex in the Organic Phase.

| Formulation | Co-solvent in Organic Phase | Median particle size | Core load (encaps. eff.) | Burst (Acylated) |
|---|---|---|---|---|
| G | MeOH (100 µL) | 11.4 µm | 0.61% (6.1%) | 20.3% (49%) |
| H | MeOH (100 µL) | 12.4 µm | 0.75% (7.5%) | 21.2% (40%) |
| I | MeOH (200 µL) | 12.9 µm | 2.64% (2.6%) | 20.2% (42%) |

Benzoic Acid.

Formulations (J-M) were prepared using one to ten equivalents of benzoic acid co-dissolved in the organic phase with PLGA. PLGA polymer (MW 24,000,180 mg) and benzoic acid (2.4-24 mg) were dissolved in EtOAc (900 µL). Octreotide acetate was dissolved in MeOH (100 µL) and added to the polymer solution yielding a homogeneous organic phase. The resulting organic phase was added to an aqueous phase (2 mL) containing 1% PVA and the mixture was vortexed for 15-30 seconds. The emulsion was poured into a solvent extraction solution (10 mM sodium phosphate, pH 8.0, 150 mL) and stirred for four hours to extract EtOAc. Particles were isolated by filtration, washed with water and air dried overnight. The core loads measured between 0.88-1.67% over the range of 1-10 added equivalents of benzoic acid per equivalent of octreotide acetate (Table 4).

Pamoic Acid.

An octreotide-pamoate complex was prepared by dissolving pamoic acid (19.4 mg, 0.05 mmol) in 0.2 N NaOH (500 µL) to provide the sodium pamoate salt. Octreotide acetate (100 mg, 0.10 mmol) was dissolved in deionized water (100 µL) and added drop wise with gentle vortexing to the sodium pamoate salt solution. This produced a flocculent light yellow precipitate. The precipitate was pelleted by centrifugation, and the supernatant removed by pipette. The pellet was washed with water (1.0 mL), re-suspended in water and lyophilized to a light yellow powder (113 mg). The octreotide/pamoate ratio of this preparation was 1.71 as measured by RP-HPLC.

A second octreotide-pamoate complex was prepared by dissolving pamoic acid (19.4 mg, 0.05 mmol) in 0.4 N NaOH (250 µL) and dioxane (250 µL) to provide a solution of sodium pamoate in dioxane/water (1:1). Octreotide acetate (50 mg, 0.05 mmol) was dissolved in dioxane/water (1:1, 200 µL). The octreotide acetate solution was added drop wise to the sodium pamoate with mixing to provide a light yellow, homogenous solution. This material was lyophilized to dryness providing a light yellow powder (65 mg). The octreotide/pamoate ratio of this preparation was 1.02 as measured by RP-HPLC. These two preparations were used to prepare new PLGA microparticle formulations.

TABLE 4

Benzoic Acid and Octreotide Acetate in Organic Phase.

| Formulation | Co-solvent in Organic Phase | Benzoic acid:Octreotide acetate ratio | Median particle size | Core load (encaps. eff.) |
|---|---|---|---|---|
| J | MeOH (100 µL) | 1 | 21.8 µm | 1.36% (14%) |
| K | MeOH (100 µL) | 2 | 19.5 µm | 0.88% (8.8%) |
| L | MeOH (100 µL) | 5 | 18.8 µm | 1.61% (16%) |
| M | MeOH (100 µL) | 10 | 17.9 µm | 1.67% (17%) |

Microparticle formulations (Table 5, Q-W) were prepared by an oil-in-water emulsion/solvent extraction method. PLGA polymer (MW 24,000, 180 mg) was dissolved in EtOAc (1000 µL). Octreotide pamoate (20 or 40 mg) was dissolved in benzyl alcohol (BnOH, 1000 µL) and added to the polymer solution yielding a homogeneous organic phase. The resulting organic phase was combined with a 1% PVA aqueous phase in a ratio of 1:2 to provide an emulsion. The emulsion was collected directly into a 0.3% PVA solvent extraction solution (150 mL) and stirred for four hours to extract EtOAc. Hardened microparticles were collected by filtration, washed with water, air dried and stored at 4° C.

Formulation characterization (Table 5) revealed that the initial octreotide/pamoate ratio of 1.7 had little effect on the encapsulation efficiency and core load relative to the formulations prepared with the octreotide/pamoate ratio of 1.02. In contrast, changing the co-solvent to benzyl alcohol increased the encapsulation efficiency by approximately 60% relative to methanol (e.g. Formulation S compared to T).

The in vitro release profiles of these formulations in PBS demonstrated total peptide released (79-92%, Table 5 Q-T) is comparable to PLGA octreotide acetate microparticles made by conventional methods (formulations D, F, Table 1) while the amount of acylated peptide released (28-40%, Table 5 Q-T) is decreased slightly relative to conventional formulations (44-55%, Table 1, A-D).

Formulations prepared using the octreotide/pamoate ratio of 1:1 did not show as strong a dependence of encapsulation efficiency and core load on the nature of the co-solvent as the 1.7 ratio formulations above. The differences in solubility for the complexes with different octreotide/pamoate ratios in the co-solvent is proposed as an explanation for this observation. The higher octreotide/pamoate ratio material had an increased solubility in benzyl alcohol relative to methanol resulting in higher encapsulation efficiency. In contrast, it was found that there was no significant difference in solubility in methanol versus benzyl alcohol for the 1:1 octreotide/pamoate complex. This resulted in similar encapsulation efficiencies and core loads independent of the co-solvents.

The in vitro release profiles of these 1:1 formulations (U-W) reveal similar trends as discussed above, namely, that the total percent of peptide released (85-110%, Table 5 U-W) is again comparable to conventional formulations (Example 1) (ca. 85%, Table 2) while the amount of acylated product released (35-44% Table 5 U-W) is decreased somewhat relative to conventional formulations (44-55%, Table 1, A-D2).

Analysis of the final octreotide/pamoate molar ratio showed a wide variation among the formulations tested (Table 5) with a range from 2.1:1 (formulation W) to over 200:1 (formulation R). In all cases the ratio is more than twice the octreotide/pamoate ratio of the starting peptide salt complex. Thus the use of a preformed pamoate salt of the peptide octreotide yielded highly variable octreotide/pamoate molar ratios in the final sustained release formulation.

(MW 24,000, 140-180 mg) was dissolved in EtOAc (1000 μL). Octreotide acetate (20-60 mg) was dissolved in BnOH (1000 μL) and added to the polymer solution yielding a homogenous organic phase. The resulting organic phase was combined with a 1% PVA aqueous phase containing 10-50 mM disodium pamoate to provide an emulsion. The emulsion was collected directly into a 0.3% PVA solvent extraction solution (150 mL) and stirred for four hours to extract EtOAc. Hardened microparticles were collected by filtration, washed with water, air dried and stored at 4° C. This resulted in a final octreotide/pamoate ratio of approximately 1-1.5 in the microparticle formulation measured by RP-HPLC (Table 6).

The effects of various experimental parameters on core load were investigated including organic to aqueous phase ratio, nature of co-solvent, and volume of co-solvent. BnOH was found to be a more suitable co-solvent than MeOH. It was possible to use BnOH in larger volumes than MeOH, as MeOH induced polymer precipitation in the organic phase. BnOH also led to a small increase in core load versus MeOH (Formulation Y, AB, Table 6). However, the use of BnOH without the organic ion in the aqueous phase did not provide high core loads or encapsulation efficiencies (AI, Table 6). It was also found that decreasing the organic to aqueous phase ratio increased the encapsulation efficiency slightly when BnOH was used as the co-solvent (Formulations AE, AF, Table 6). In all cases the molar ratio of octreotide to pamoate was tightly grouped between about 1.0 and 1.5, in contrast to the formulations of Example 2 (Table 5) where the use of a

TABLE 5

Octreotide-Pamoate Microparticles Prepared Using Pre-Formed Complex.

| Formulation | Octreotide/ pamoate ratio initial (final) | Co-solvent in Organic Phase | Median particle size | Core load (encap eff) | Total Peptide Release (Acylated) |
|---|---|---|---|---|---|
| Q | 1.7:1 (4.4:1) | MeOH (100 μL) | 40 μm | 6.52% (65%) | 88.6% (28.1%) |
| R | 1.7:1 (201:1) | MeOH (500 μL) | 34 μm | 3.34% (33%) | 79.2% (38.9%) |
| S | 1.7:1 (13:1) | BnOH (200 μL) | 31 μm | 8.29% (83%) | 87.2% (39.7%) |
| T | 1.7:1 (21:1) | MeOH (200 μL) | 37 μm | 5.03% (50%) | 91.5% (32.2%) |
| U | 1:1 (5.3:1) | MeOH (200 μL) | 48 μm | 4.93% (49%) | 92.3% (37.3%) |
| V | 1:1 (5.4:1) | BnOH (200 μL) | 48 μm | 4.76% (48%) | 110% (44.4%) |
| W | 1:1 (2.1:1) | BnOH (200 μL) | 44 μm | 5.01% (25%) | 84.9% (35.0%) |

Example 3

Octreotide Acetate Encapsulation in PLGA Microspheres Using Organic Acid Salts in the Aqueous Emulsion Phase According to the Present Invention Surprisingly it was discovered that the use of an organic acid salt in the aqueous phase of the emulsification process allowed use of a water soluble peptide and eliminated the need to prepare complexed species in an independent step prior to preparing the formulation. The present invention provided added benefits such as increased drug coreload, consistent octreotide/organic ion ratio, and decreased peptide degradation during in vitro release.

Microparticle formulations were prepared by an oil-in-water emulsion/solvent extraction method. PLGA polymer preformed octreotide/pamoate complex led to wide variations of the final octreotide/pamoate ratio from 2.1 to over 200.

Significantly, product with predictable and elevated drug core loads ranging from 5-17.5% could be formed with the method of the present invention, (formulations AD, AG, AH, Table 6), in contrast to the prior art methods of Examples 1 and 2 where the maximum drug core load achieved was about 8% (Table 5-S) with averages ranging from 2-6% (Tables 1-5). In addition, the compositions of the present invention have consistent stoichiometry for the molar ratio of bioactive agent to organic ion (Table 6). This is in contrast to the compositions made using previous methods (Table 5). Furthermore, the relative production of acylated peptide is lower for microparticles made with the organic ion in the aqueous phase (Table 6) than for microparticles made with the use of preformed octreotide-pamoate (Table 5) or octreotide acetate (Table 2).

TABLE 6

Octreotide-Pamoate Complex Microparticles by an in situ Process.

| Formulation (Octreotide/pamoate final ratio) | Octreotide acetate input | Co-solvent | Organic/Aqueous phase ratio | Median particle size | Core load (encap eff) | Total Peptide Release (Acylated) |
|---|---|---|---|---|---|---|
| X (1.09:1) | 40 mg | MeOH (200 µL) | 1:4 | 79 µm | 8.52% (46.8%) | 98.8% (15.7%) |
| Y (0.86:1) | 20 mg | MeOH (200 µL) | 1:10 | 71 µm | 5.13% (51%) | 120% (30.6%) |
| Z (1.09:1) | 20 mg | BnOH (1000 µL) | 1:2 | 44 µm | 7.61% (76%) | 97.1% (4.11%) |
| AA (1.01:1) | 20 mg | BnOH (1000 µL) | 1:2 | 59 µm | 6.79% (6.8%) | 101% (12.7%) |
| AB (1.11:1) | 20 mg | BnOH (500 µL) | 1:2 | 45 µm | 6.19% (62%) | 97.1% (14.8%) |
| AC (1.14:1) | 20 mg | BnOH (1000 µL) | 1:2 | 47 µm | 7.51% (75%) | 96.8% (13.4%) |
| AD (1.11:1) | 40 mg | BnOH (1000 µL) | 1:2 | 53 µm | 12.7% (64%) | 101% (16.1%) |
| AE (1.41:1) | 60 mg | BnOH (500 µL) | 1:2 | 45 µm | 9.51% (32%) | 103% (26.1%) |
| AF (1.16:1) | 60 mg | BnOH (500 µL) | 1:4 | 50 µm | 12.0% (40%) | 108% (21.7%) |
| AG (1.39:1) | 60 mg | BnOH (1000 µL) | 1:2 | 39 µm | 17.2% (57%) | 92.5% (20.7%) |
| AH (1.36:1) | 60 mg | BnOH (1000 µL) | 1:2 | 37 µm | 17.5% (57%) | 111% (25.0%) |
| AI | 60 mg | BnOH (1000 µL) | 1:2 | 40 µm | 6.85% (23%) | ND |

The effect of organic acid concentration in the aqueous phase was explored to determine the optimal manufacturing parameters. PLGA polymer (MW 24,000, 160 mg) was dissolved in EtOAc (1000 µL). Octreotide acetate (40 mg) was dissolved in BnOH (1000 µL) and added to the polymer solution yielding a homogenous organic phase. The resulting organic phase was combined with a 1% PVA aqueous phase containing 20 or 50 mM sodium pamoate to provide an emulsion. The emulsion was collected directly into a 0.3% PVA solvent extraction solution (150 mL) and stirred for four hours to extract EtOAc. Hardened microparticles were collected by filtration, washed with water, air dried and stored at 4° C. Formulations AJ-AL show that 20 or 50 mM disodium pamoate had no effect on core load relative to 10 mM disodium pamoate (Table 7). However, the disodium pamoate concentration in the aqueous phase did have a measurable effect on the "day one" in vitro PBS release. The formulation prepared using 50 mM disodium pamoate resulted in a 15% burst (Formulation AL, Table 7) as compared to less than 4% burst for formulations prepared with 20 mM organic ion (Formulations AJ, AK, Table 7). This suggests that excess organic ion in the aqueous phase is deleterious to the in vitro release performance of the formulations.

TABLE 7

The effect of organic ion concentration on the formation of octreotide-pamoate microparticles.

| Formulation (Octreotide/pamoate final ratio) | Sodium pamoate conc | Organic/Aqueous phase ratio | Median particle size | Core load (encap eff) | PBS Burst Release | Total Peptide Release (Acylated) |
|---|---|---|---|---|---|---|
| AJ (1.33:1) | 20 mM | 1:1 | 33 µm | 13.3% (67%) | 3.77% | 108% (25.7%) |
| AK (1.29:1) | 20 mM | 1:2 | 41 µm | 13.3% (67%) | 3.38% | 106% (22.4%) |
| AL (1.29:1) | 50 mM | 1:2 | 54 µm | 12.8% (64%) | 15.0% | 110% (26.8%) |

Alternative organic ions in addition to pamoate were investigated to explore the general utility of the present invention. Microparticle formulations were prepared by an oil-in-water emulsion/solvent extraction method. PLGA polymer (MW 24,000, 160 mg) was dissolved in EtOAc (1000 µL). Octreotide acetate (40 mg) was dissolved in BnOH (1000 µL) and added to the polymer solution yielding a homogenous organic phase. The resulting organic phase was combined with a 1% PVA aqueous phase containing 10-20 mM organic acid as its sodium salt to provide an emulsion. The emulsion was collected directly into a 0.3% PVA solvent extraction solution (150 mL) and stirred for four hours to extract EtOAc. Hardened microparticles were collected by filtration, washed with water, air dried and stored at 4° C. This resulted in microparticle formulations with octreotide core loads between 6.8 and 15.3% as measured by RP-HPLC (Table 8). The effects of the tested organic ions on core load are revealing. Formulations AM-AP show no increase in the measured core load relative to control containing sodium pamoate (Formulations AT, AU, AY, Table 8). In contrast formulations AQ-AS, AV-AX and AZ-BB, which employed organic acids ranging from cholic acid to bicyclic aromatics, provided peptide core loads comparable to pamoic acid (Table 8). These results imply that organic acids with appropriate physiochemical properties can be substituted for pamoic acid to produce comparable microparticle formulations.

TABLE 8

The effect of various organic acids (sodium salts) in the aqueous phase on the formation of octreotide-complex microparticles.

| Formulation | Organic acid sodium salt (conc.) | Particle size | Core load (encap eff) | Total Peptide Release (Acylated) |
|---|---|---|---|---|
| AM | Succinic (10 mM) | 34.1 μm | 7.74% (39%) | 99.9% (53.4%) |
| AN | Benzoic (10 mM) | 32 μm | 6.88% (34%) | 105% (56.7%) |
| AO | Salicylic (10 mM) | 34 μm | 7.78% (39%) | 106% (54.0%) |
| AP | Trifluoromethyl-p-toluic (10 mM) | 33 μm | 8.92% (45%) | 107% (50.7%) |
| AQ | Cholic (20 mM) | 60 μm | 13.2% (66%) | 104% (47.2%) |
| AR | 2-Naphthalene sulfonic (20 mM) | 38 μm | 11.6% (58%) | 110% (42.6%) |
| AS | 2,3-Naphthalene dicarboxylic (10 mM) | 38 μm | 13.1% (66%) | 109% (47%) |
| AT | Pamoic (10 mM) | 45 μm | 13.8 (69%) | 98.5% (37%) |
| AU | Pamoic (10 mM) | 43 μm | 14.2% (71%) | 97.5% (31%) |
| AV | 1-Hydroxy-2-naphthoic (20 mM) | 42 μm | 15.3% (76%) | 152% (25.7%) |
| AW | 3-Hydroxy-2-naphthoic (20 mM) | 40 μm | 14.6% (72%) | 105% (20.8%) |
| AX | 2-Naphthoic (20 mM) | 39 μm | 13.4% (67%) | 134% (32.9%) |
| AY | Pamoic (10 mM) | 46 μm | 14.4% (72%) | 103% (22%) |
| AZ | 2-Naphthalene sulfonic (20 mM) | 36 μm | 10.8% (54%) | 138% (33.0%) |
| BA | 2,3-Naphthalene dicarboxylic (10 mM) | 46 μm | 12.1% (61%) | 97.8% (25%) |
| BB | Salicylsalicylic (20 mM) | 39 μm | 12.4% (62%) | 114% (23.2%) |

Example 4

Encapsulation of Additional Peptides in PLGA Microspheres Using Organic Acid Salts in the Aqueous Emulsion Phase According to the Present Invention Oxytocin acetate and leuprolide acetate were formulated in PLGA microparticles according to the present invention as described in the examples below. The results of these investigations demonstrate the utility of the present invention in relation to increased core load and encapsulation efficiency (Formulations BI vs BJ-BK and BL vs BM) relative to conventional methodology (Table 9).

Formulation BI (Leuprolide)—Conventional Encapsulation Method

PLGA polymer (MW 24,000, 160 mg) was dissolved in $CH_2Cl_2$ (1000 μL). Leuprolide acetate (40 mg) was dissolved in BnOH (1000 μL) and added to the polymer solution yielding a homogeneous organic phase. The resulting organic phase was combined with a 1% PVA aqueous phase to provide an emulsion. The emulsion was collected directly into a 0.3% PVA solvent extraction solution (150 mL) and stirred for four hours to extract EtOAc. Hardened microparticles were collected by filtration, washed with water, air dried and stored at 4° C. This provided formulation BI (140 mg, 70.0% yield) with a median particle size 50.1 μm. The core load (1.99%), encapsulation efficiency (9.95%) and in vitro burst (1.63%) were determined by RP-HPLC assay.

Formulation BJ (Leuprolide)—Organic Ion Assisted Encapsulation Method

PLGA polymer (MW 24,000, 160 mg) was dissolved in $CH_2Cl_2$ (1000 μL). Leuprolide acetate (40 mg) was dissolved in BnOH (1000 μL) and added to the polymer solution yielding a homogeneous organic phase. The resulting organic phase was combined with a 1% PVA aqueous phase containing 10 mM disodium pamoate to provide an emulsion. The emulsion was collected directly into a 0.3% PVA solvent extraction solution (100 mL) and stirred for 10 minutes. A secondary extraction solution consisting of 2% isopropanol (200 mL) was added and stirred for an additional four hours. Hardened microparticles were collected by filtration, washed with water, air dried and stored at 4° C. This provided formulation BJ (157 mg, 78.5% yield) with a median particle size 54.0 μm. The core load (9.4%), encapsulation efficiency (47.0%) and in vitro burst (5.31%) were determined by RP-HPLC assay.

Formulation BK (Leuprolide)—Organic Ion Assisted Method

A microparticle formulation was prepared by an oil-in-water emulsion/solvent extraction method. PLGA polymer (MW 24,000, 160 mg) was dissolved in $CH_2Cl_2$ (1000 μL). Leuprolide acetate (40 mg) was dissolved in BnOH (1000 μL) and added to the polymer solution yielding a homogeneous organic phase. The resulting organic phase was combined with a 1% PVA aqueous phase containing 50 mM disodium pamoate to provide an emulsion. The emulsion was collected directly into a 0.3% PVA solvent extraction solution (100 mL) and stirred for 10 minutes. A secondary extraction solution consisting of 2% isopropanol (200 mL) was added and stirred for an additional four hours. Hardened microparticles were collected by filtration, washed with water, air dried and stored at 4° C. This provided formulation BK (120 mg, 60.0% yield) with a median particle size 43.1 µm. The core load (10.6%), encapsulation efficiency (53.0%) and in vitro burst (21.1%) were determined by RP-HPLC assay.

Formulation BL (Oxytocin)—Conventional Encapsulation Method

PLGA polymer (MW 13,000, 180 mg) was dissolved in EtOAc (900 µL). Oxytocin acetate (20 mg) was dissolved in MeOH (100 µL) and added to the polymer solution yielding a milky suspension as the organic phase. The resulting organic phase was combined with a 1% PVA aqueous phase containing 5% EtOAc to provide an emulsion. The emulsion was collected directly into a 10 mM sodium phosphate (pH 8, 0° C., 150 mL) solvent extraction solution and stirred for four hours while warming to room temperature to extract EtOAc. Hardened microparticles were collected by filtration, washed with water, air dried and stored at 4° C. This provided formulation BL (143 mg, 71.5% yield) with a median particle size 44.0 µm. The core load (1.67%), encapsulation efficiency (16.7%) and in vitro burst (46.3%) were determined by RP-HPLC assay.

Formulation BM (Oxytocin)—Organic Ion Assisted Encapsulation Method

PLGA polymer (MW 24,000, 180 mg) was dissolved in EtOAc (1800 µL). Oxytocin acetate (40 mg) was dissolved in MeOH (200 µL) and added to the polymer solution yielding a milky suspension as the organic phase. The resulting organic phase was combined with a 1% PVA aqueous phase containing 10 mM disodium pamoate to provide an emulsion. The emulsion was collected directly into a 0.3% PVA solvent extraction solution (150 mL) and stirred for four hours to extract EtOAc. Hardened microparticles were collected by filtration, washed with water, air dried and stored at 4° C. This provided formulation BM (158 mg, 79.0% yield) with a median particle size 144 µm. The core load (8.9%), encapsulation efficiency (44.5%) and in vitro burst (21.1%) were determined by RP-HPLC assay.

TABLE 9

Peptide-pamoate complex microparticles by an in situ process.

| Formulation | Peptide | Pamoate conc. | Core load | Encap. Eff. |
|---|---|---|---|---|
| BI | leuprolide | 0 mM | 2.0% | 10.0% |
| BJ | leuprolide | 10 mM | 9.4% | 47.0% |
| BK | leuprolide | 50 mM | 10.6% | 53.0% |
| BL | oxytocin | 0 mM | 1.7% | 16.7% |
| BM | oxytocin | 10 mM | 8.9% | 49.1% |

Example 5

Insulin Encapsulation in PLGA Microparticles Using Organic Acid Salts in the Aqueous Emulsion Phase Sodium Dodecylsulfate Microparticle formulations were prepared using an oil-in-water emulsion/solvent extraction method. The organic phase consisted of PLGA polymer (MW 11,800, 150 mg) and PEGylated-insulin (50 mg) dissolved in $CH_2Cl_2$ (2 mL). The aqueous phase consisted of 1% PVA and 14 mM SDS. The homogeneous organic and aqueous phases were combined in a ratio of 1:5 to produce an organic in aqueous phase emulsion. The emulsion was collected directly into a 0.3% PVA solvent extraction solution (100 mL) and stirred for 10 minutes before adding 100 mL 2% IPA. The solvent extraction solution was then stirred for an additional 3 hours to extract $CH_2Cl_2$. Hardened microparticles were collected by filtration, washed with water, air dried and stored at −20° C. The resulting microparticle had a core load of 21% (encapsulation efficiency 84%). These microparticles were characterized by a large in vitro burst of 50% at 24 h in PBS at 37° C.

Disodium Pamoate

Microparticle formulations were prepared using an oil-in-water emulsion/solvent extraction method. The organic phase consisted of PLGA polymer (MW 11,800, 75 mg) and PEGylated-insulin (25 mg) dissolved in $CH_2Cl_2$ (1 mL). The aqueous phase consisted of 1% PVA and 10 mM disodium pamoate. The homogeneous organic and aqueous phases were combined in a ratio of 1:5 to produce an organic in aqueous phase emulsion. The emulsion was collected directly into a 0.3% PVA solvent extraction solution (50 mL) and stirred for 10 minutes before adding water (100 mL). The solvent extraction solution was then stirred for an additional 3 hours to extract $CH_2Cl_2$. Hardened microparticles were collected by filtration, washed with water, air dried and stored at −20° C. The resulting microparticles had a core load of 18% (encapsulation efficiency 78%) and a final PEGylated-insulin/pamoate ratio of 1:2. In contrast to the microparticles made with SDS, these microparticles had a low in vitro burst of 5% in PBS at 37° C.

Example 6

Evaluation of the Pharmacokinetics of Octreotide in PLGA Microparticles after Administration to Sprague Dawley Rats Blood serum levels were measured for octreotide released from PLGA microparticle formulations injected subcutaneously in rats. Animals (n=6/group) were treated once by subcutaneous injection of a single dose level (~8-10 mg/kg) of six different octreotide PLGA microparticle formulations. At hours 1 and 6, and on days 1, 4, 7, 11, 14, 20, 28, 42 and 54, serum samples were obtained from each animal to evaluate the octreotide pharmacokinetics. Serum concentrations were measured by a commercially available extraction-free radioimmunoassay kit (#S-2211) (Peninsula Labs). The Limit of Quantitation (LOQ) of the assay was 0.1 ng/mL. The mean octreotide serum concentrations for each time point are reported in Table 10. The preparation of the octreotide PLGA formulations tested is described below.

TABLE 10

Mean octreotide serum levels (ng/mL) after a single subcutaneous treatment in rats.

| Formulation | Dose (mg/Kg) | Sample Day | | | | | | | | | | | |
|---|---|---|---|---|---|---|---|---|---|---|---|---|---|
| | | 0 | 0.04 | 0.25 | 1 | 4 | 7 | 11 | 14 | 20 | 28 | 42 | 54 |
| BC | 10.2 | 0.00 | 39.75 | 3.83 | 0.62 | 1.44 | 3.07 | 3.71 | 3.42 | 3.51 | 1.95 | 0.39 | 0.00 |
| BD | 8.9 | 0.00 | 39.95 | 4.00 | 0.95 | 1.66 | 3.41 | 3.64 | 3.44 | 2.03 | 1.04 | 0.45 | 0.00 |
| BE | 9.7 | 0.00 | 36.35 | 4.09 | 2.04 | 2.13 | 2.59 | 2.89 | 2.94 | 2.19 | 1.81 | 3.09 | 0.90 |
| BF | 8.6 | 0.00 | 39.75 | 3.89 | 1.33 | 2.54 | 3.06 | 3.16 | 2.89 | 1.43 | 0.64 | 1.52 | 0.00 |
| BG | 9.2 | 0.00 | 29.70 | 3.82 | 2.06 | 1.85 | 2.28 | 1.96 | 2.00 | 1.70 | 0.97 | 2.24 | 1.39 |
| BH | 9.4 | 0.00 | 39.80 | 4.13 | 2.90 | 3.70 | 3.64 | 3.54 | 3.44 | 2.34 | 1.70 | 1.63 | 0.05 |

Preparation and Characterization of Octreotide Formulations Used in the Animal Study.

Formulation BC

PLGA polymer (MW 24,000, 720 mg) was dissolved in EtOAc (4000 µL). Octreotide acetate (80 mg) was dissolved in BnOH (4000 µL) and added to the polymer solution yielding a homogeneous organic phase. The resulting organic phase was combined with a 1% PVA aqueous phase containing 10 mM disodium pamoate to provide an emulsion. The emulsion was collected directly into a 0.3% PVA solvent extraction solution (600 mL) and stirred for four hours to extract EtOAc. Hardened microparticles were collected by filtration, washed with water, air dried and stored at 4° C. This provided formulation BC (754 mg, 94% yield) with a median particle size 55.0 µm. The core load (8.5%), encapsulation efficiency (85.0%) and in vitro burst (7.4%) were determined by RP-HPLC assay.

Formulation BD

PLGA polymer (MW 24,000, 680 mg) was dissolved in EtOAc (4000 µL). Octreotide acetate (120 mg) was dissolved in BnOH (4000 µL) and added to the polymer solution yielding a homogeneous organic phase. The resulting organic phase was combined with a 1% PVA aqueous phase containing 10 mM disodium pamoate to provide an emulsion. The emulsion was collected directly into a 0.3% PVA solvent extraction solution (600 mL) and stirred for four hours to extract EtOAc. Hardened microparticles were collected by filtration, washed with water, air dried and stored at 4° C. This provided formulation BD (694 mg, 94% yield) with a median particle size 58.7 µm. The core load (11.8%), encapsulation efficiency (78.7%) and in vitro burst (4.1%) were determined by RP-HPLC assay.

Formulation BE

PLGA polymer (MW 24,000, 680 mg) was dissolved in EtOAc (4000 µL). Octreotide acetate (120 mg) was dissolved in BnOH (4000 µL) and added to the polymer solution yielding a homogeneous organic phase. The resulting organic phase was combined with a 1% PVA aqueous phase containing 10 mM disodium pamoate to provide an emulsion. The emulsion was collected directly into a 0.3% PVA solvent extraction solution (600 mL) and stirred for four hours to extract EtOAc. Hardened microparticles were collected by filtration, washed with water, air dried and stored at 4° C. This provided formulation BE (727 mg, 91% yield) with a median particle size 52.2 µm. The core load (11.6%), encapsulation efficiency (77.3%) and in vitro burst (2.75%) were determined by RP-HPLC assay.

Formulation BF

PLGA polymer (MW 24,000, 640 mg) was dissolved in EtOAc (4000 µL). Octreotide acetate (160 mg) was dissolved in BnOH (4000 µL) and added to the polymer solution yielding a homogeneous organic phase. The resulting organic phase was combined with a 1% PVA aqueous phase containing 10 mM disodium pamoate to provide an emulsion. The emulsion was collected directly into a 0.3% PVA solvent extraction solution (600 mL) and stirred for four hours to extract EtOAc. Hardened microparticles were collected by filtration, washed with water, air dried and stored at 4° C. This provided formulation BF (766 mg, 95.8% yield) with a median particle size 47.7 µm. The core load (14.7%), encapsulation efficiency (73.5%) and in vitro burst (5.5%) were determined by RP-HPLC assay.

Formulation BG

PLGA polymer (MW 28,000, 640 mg) was dissolved in EtOAc (4000 µL). Octreotide acetate (160 mg) was dissolved in BnOH (4000 µL) and added to the polymer solution yielding a homogeneous organic phase. The resulting organic phase was combined with a 1% PVA aqueous phase containing 10 mM disodium pamoate to provide an emulsion. The emulsion was collected directly into a 0.3% PVA solvent extraction solution (600 mL) and stirred for four hours to extract EtOAc. Hardened microparticles were collected by filtration, washed with water, air dried and stored at 4° C. This provided formulation BG (715 mg, 89.3% yield) with a median particle size 48.7 µm. The core load (11.9%), encapsulation efficiency (59.5%) and in vitro burst (2.3%) were determined by RP-HPLC assay.

Formulation BH

PLGA polymer (MW 14,000, 560 mg) was dissolved in EtOAc (4000 µL). Octreotide acetate (240 mg) was dissolved in BnOH (4000 µL) and added to the polymer solution yielding a homogeneous organic phase. The resulting organic phase was combined with a 1% PVA aqueous phase containing 10 mM disodium pamoate to provide an emulsion. The emulsion was collected directly into a 0.3% PVA solvent extraction solution (600 mL) and stirred for four hours to extract EtOAc. Hardened microparticles were collected by filtration, washed with water, air dried and stored at 4° C. This provided formulation BH (680 mg, 85.0% yield) with a median particle size 40.6 µm. The core load (17.4%), encapsulation efficiency (58.0%) and in vitro burst (6.8%) were determined by RP-HPLC assay.

All of the compositions and methods disclosed and claimed herein can be made and executed without undue experimentation in light of the present disclosure. While the compositions and methods of this invention have been described in terms of particular embodiments, it will be apparent to those of skill in the art that variations may be applied to the compositions, and methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

I claim:

1. A composition comprising a bioactive agent and a biodegradable polymer in an organic phase; and an organic ion in an aqueous phase that forms a complex with the bioactive agent,
   wherein the organic ion comprises trifluoromethyl-p-toluate, 2-naphthalene sulfonate, 2,3-naphthalene dicarboxylate, 1-hydroxy-2-naphthoate, 3-hydroxy-2-naphthoate, 2-naphthoate, or salicylsalicylate, or a mixture thereof, and
   wherein the stoichiometry of the bioactive agent relative to the organic ion ranges from about 1.0 to 1.5.

2. The composition of claim 1, wherein said biodegradable polymer comprises poly(lactide)s, poly(glycolide)s, poly(lactide-co-glycolide)s, poly(lactic acid)s poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol or polyorthoester, biodegradable polyurethanes, blends or copolymers thereof.

3. The composition of claim 1, wherein said bioactive agent comprises proteins, nucleic acids, carbohydrates, peptides, LHRH agonists, leuprolide, oxytocin, somatostatin, small molecule pharmaceutical substances, immunogens, metabolic precursors capable of promoting growth and survival of cells and tissues, antineoplastic agents, hormones, antihistamines, cardiovascular agents, anti-ulcer agents, bronchodilators, vasodilators, central nervous system agents or narcotic antagonists or a mixture thereof.

4. The composition of claim 1, wherein the bioactive agent comprises octreotide or octreotide acetate or a mixture thereof.

5. The composition of claim 1, wherein the organic ion interacts with the bioactive agent to form a charged or neutral complex.

6. The composition of claim 1, wherein the organic ion comprises trifluoromethyl-p-toluate, 2,3-naphthalene dicarboxylate, 1-hydroxy-2-naphthoate, 3-hydroxy-2-naphthoate, 2-naphthoate, or salicylsalicylate or a mixture thereof.

7. The composition of claim 1, wherein the organic phase comprises a solvent and a co-solvent.

8. The composition of claim 1, wherein the organic phase comprises methylene chloride, ethyl acetate, benzyl alcohol, acetone, acetic acid or propylene carbonate or a mixture thereof.

9. The composition of claim 7, wherein the co-solvent comprises methyl alcohol, ethyl alcohol, isopropyl alcohol, N-methyl pyrrolidinone, dimethyl sulfoxide, N,N-dimethyl formamide, PEG 200, PEG 400 or benzyl alcohol or a mixture thereof.

10. The composition of claim 1, wherein the aqueous phase comprises methanol, benzyl alcohol, isopropyl alcohol, water, dimethylsulfoxide, N,N-dimethylformamide or methylene chloride, or mixtures thereof.

11. The composition of claim 1, wherein the composition produces a controlled release composition.

12. The composition of claim 11, wherein said controlled release composition comprises microparticles or nanoparticles or a mixture thereof.

13. The composition of claim 12, wherein said microparticles and nanoparticles are biodegradable.

* * * * *